US010500308B2

(12) United States Patent
Flynn

(10) Patent No.: US 10,500,308 B2
(45) Date of Patent: Dec. 10, 2019

(54) DECELLULARIZED ADIPOSE TISSUE

(71) Applicant: Queen's University at Kingston, Kingston (CA)

(72) Inventor: Lauren E. Flynn, London (CA)

(73) Assignee: Queen's University at Kingston, Kingston, ON (CA)

(*) Notice: Subject to any disclaimer, the term of this patent is extended or adjusted under 35 U.S.C. 154(b) by 417 days.

(21) Appl. No.: 14/710,964

(22) Filed: May 13, 2015

(65) Prior Publication Data

US 2016/0051728 A1 Feb. 25, 2016

Related U.S. Application Data

(62) Division of application No. 12/971,531, filed on Dec. 17, 2010, now Pat. No. 9,034,386.

(Continued)

(51) Int. Cl.
*A61L 27/36* (2006.01)
*A61L 27/50* (2006.01)
(Continued)

(52) U.S. Cl.
CPC ....... *A61L 27/3604* (2013.01); *A61L 27/3683* (2013.01); *A61L 27/3834* (2013.01);
(Continued)

(58) Field of Classification Search
CPC ............. A61K 2300/64; A61L 2430/40; A61L 27/3604; A61L 27/3683; A61L 27/3834;
(Continued)

(56) References Cited

U.S. PATENT DOCUMENTS 6,777,231 B1   8/2004   Katz et al.
7,470,537 B2   12/2008  Hedrick et al.
(Continued)

FOREIGN PATENT DOCUMENTS

WO   WO 2003/022988 A2   3/2003
WO   WO 2006/095342 A2   9/2006
(Continued)

OTHER PUBLICATIONS

Lodish et al, "Section 22.3 Collagen: The Fibrous Proteins of the Matrix," Molecular Cell Biology, 4th edition, New York, W.H. Freeman, 2000, pp. 1-6.*

(Continued)

*Primary Examiner* — Rachael E Bredefeld
(74) *Attorney, Agent, or Firm* — Stephen J. Scribner

(57) ABSTRACT

This invention provides a method for decellularizing adipose tissue, comprising subjecting the adipose tissue to one or more incubations in an enzymatic digestion solution containing one or more enzymes, and one or more solvent extractions, wherein decellularized adipose tissue comprising an extracellular matrix with well-preserved three-dimensional structure is obtained. The invention also provides a decellularized adipose tissue comprising an extracellular matrix with well-preserved three-dimensional architecture, and bioscaffolds, microcarrier beads, and coatings comprising the decellularized adipose tissue.

30 Claims, 14 Drawing Sheets

Specification includes a Sequence Listing.

Related U.S. Application Data

(60) Provisional application No. 61/287,236, filed on Dec. 17, 2009.

(51) Int. Cl.
*A61L 27/38* (2006.01)
*C12N 11/02* (2006.01)
*C12N 5/077* (2010.01)

(52) U.S. Cl.
CPC .......... *A61L 27/50* (2013.01); *C12N 5/0653* (2013.01); *C12N 11/02* (2013.01); *A61L 2300/64* (2013.01); *A61L 2400/04* (2013.01); *A61L 2400/06* (2013.01); *A61L 2430/40* (2013.01); *C12N 2533/90* (2013.01)

(58) Field of Classification Search
CPC .......... A61L 2300/64; C12N 2533/90; C12N 5/0653; C12N 11/02
See application file for complete search history.

(56) References Cited

U.S. PATENT DOCUMENTS

| | | |
|---|---|---|
| 9,034,386 B2 | 5/2015 | Flynn |
| 2002/0119437 A1 | 8/2002 | Grooms et al. |
| 2003/0162707 A1 | 8/2003 | Fraser et al. |
| 2005/0013870 A1 | 1/2005 | Freyman et al. |
| 2005/0282775 A1 | 12/2005 | Katz et al. |
| 2008/0286268 A1 | 11/2008 | Johnson |
| 2009/0202977 A1 | 8/2009 | Ott et al. |

FOREIGN PATENT DOCUMENTS

| | | |
|---|---|---|
| WO | WO 2008/154149 A2 | 12/2008 |
| WO | WO 2009/102452 A2 | 8/2009 |
| WO | WO 2011/019822 A2 | 2/2011 |

OTHER PUBLICATIONS

Gilbert, T. W., et al., "Decellularization of tissues and organs," Biomaterials, vol. 27, 3675-3683 (2006).

Flynn, L.E., "The use of decellularized adipose tissue to provide an inductive microenvironment for the adipogenic differentiation of human adipose-derived stem cells", Biomaterials, vol. 31, 4715-4724 (2010).

Brown, B., et al., "Comparison of three methods for the derivation of a biologic scaffold composed of adipose tissue extracellutar matrix," Tissue Engineering Part C Methods, 1-33 (2010).

PCT International Search Report for International Application No. PCT/CA2010/002010 filed on Dec. 17, 2010.

PCT Written Opinion of the International Searching Authority for International Application No. PCT/CA2010/002010 filed on Dec. 17, 2010.

Young, D. Adam, et al., "Injectable hydrogel scaffold from decellularized human lipoaspirate," Acta Biomaterialia, vol. 7, 1040-1049 (2011).

Extended European Search Report for EP10836896.0 dated Nov. 13, 2013.

Office Action dated May 21, 2014 for Chinese Patent Application No. 201080064286.X.

Office Action dated Feb. 13, 2015 for Chinese Patent Application No. 201080064286.X.

\* cited by examiner

SEQUENCE LISTING

<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
ttcagaaatg ccttgcagtg                                        20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
ccaacagctt ctccttctcg                                        20

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
cagagggacc ggagttatga                                        20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
ttcacattgc acaaggcact                                        20

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
gtccgtggct acctgtcatt                                        20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tggcacccaa ctctcataca                                        20

<210> SEQ ID NO 7
<211> LENGTH: 20
<212> TYPE: DNA
<213> ORGANISM: Artificial sequence

```
<220> FEATURE:
<223> OTHER INFORMATION: Primer

<400> SEQUENCE: 7
aagaggaagg ccaagtcgag                                              20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
cacacgtctc ggtcatggta                                              20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
tctaccccaa tccagcaaac                                              20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gttgggagcc agattgtcat                                              20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
ggtattccag gatgcaatgg                                              20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gcacatggcc aagtatctca                                              20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
acagtcagcc gcatcttctt                                              20
```

-continued

```
<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
acgaccaaat ccgttgactg                                              20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
agactttgga tcggttggtg                                              20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
ttaaatgcag ggacgaaagg                                              20
```

DECELLULARIZED ADIPOSE TISSUE

RELATED APPLICATION

This application is a division of application Ser. No. 12/971,531, filed on 17 Dec. 2010, now U.S. Pat. No. 9,034,386, and claims the benefit of the filing date of U.S. Provisional Patent Application No. 61/287,236, filed 17 Dec. 2009, the contents of which are incorporated herein by reference in their entirety.

FIELD OF THE INVENTION

This invention relates to a method for decellularizing adipose tissue, and to decellularized adipose tissue having extracellular matrix with well-preserved three-dimensional structure. The decellularized adipose tissue is suitable for use in biomedical applications such as in soft tissue augmentation or as a bioscaffold. In addition, the decellularized adipose tissue can be used as a cell culture substrate for primary cells or cell lines in static culture, within a bioreactor system, or in vivo.

BACKGROUND

Current clinical strategies for soft tissue augmentation primarily involve autologous, allogenic, and alloplastic biomaterials. Much of the interest in the autologous approach has focussed on transfer of adipose tissue. This approach is favourable because most patients have expendable reserves of adipose tissue available for transplantation, and the advent of liposuction has facilitated the process of tissue harvesting. However, free fat transfer yields unsatisfactory and unpredictable results, with varying degrees of graft resorption due to a lack of supporting vasculature. In general, only small defects can be corrected with injected autologous fat, and even these limited applications require repeated treatments to maintain the desired volume as the implanted fat is gradually replaced by fibrous tissue interspersed with oil cysts.

Autologous tissue transfer using vascularized flaps that incorporate skin, fat, and muscle requires considerable surgical skill, but can yield far superior results to those obtained with synthetic implants. However, the flaps have high costs in terms of donor site morbidity and deformity, as well as hospitalization and surgical time. The transfer of significant tissue volumes can also result in a weakening of the donor site, particularly in the case of major muscle transfer from the abdominal region. Autologous collagen injectables may be prepared from biopsies or larger samples of the patient's own skin. Such materials are associated with implant resorption and provide only a transient augmentation effect. The amount of tissue that can be obtained using this approach is limited by the creation of a defect in the skin.

Allogenic materials are primarily used as injectable bulking agents for small volume cosmetic applications involving wrinkles and minor defects in the face. The materials temporarily augment the dermal region, smoothing the appearance of the overlying epidermis. In general, these materials have limitations and most require repeated, expensive treatments to maintain the desired effect. Materials such as collagen derived from animal (e.g., bovine, porcine) sources may be associated with hypersensitivity and immune reaction. Rapid implant resorption is also an issue, such that overcorrection (100-200%) at the time of implantation is recommended and repeated treatments (every 3-6 months) are necessary to maintain the desired volume. Cross-linking the collagen with glutaraldehyde may improve resiliency and decrease the immunogenicity of the material. Concerns about disease transmission limit the clinical applicability of xenogenic collagens.

Other allogenic materials such as decellularized human cadaveric dermis that contains collagen, elastin, and glycosaminoglycans (GAGs) may be produced in an injectable form, or in sheets which can be cut to shape for a given application. The materials are non-immunogenic and may last up to two years; however, resorption occurs and overcorrection of up to 200% may be required.

Injectable alloplastic materials, including poly(L-lactic acid) (PLA), have been approved for the treatment of lipoatrophy in patients with HIV. Repeated injections are required and the formation of palpable nodules has been reported. Injectable polytetrafluoroethylene (PTFE) facilitates permanent augmentation without the need for multiple treatments. However, PTFE implants can migrate from the implantation site, have increased risk of infection and have significantly different mechanical properties than soft tissue.

The above autologous, allogenic, and alloplastic approaches to soft tissue augmentation suffer from substantial weaknesses. An alternative approach to soft tissue reconstruction employs a cell-seeded scaffold. Scaffolding materials may be synthetic (e.g., polylactic-co-glycolic acid, polyglycolic acid, polyethylene glycol diacrylate) or naturally-derived (e.g., collagen, fibrin, derivatives of hyaluronan, silk protein). Insofar as naturally-derived scaffolding biomaterials may be preferred, a potential drawback is that they require processing, such as decellularization, prior to use to minimize the potential for immunogenic reaction and to ensure long-term stability.

SUMMARY

Described herein is a method for decellularizing adipose tissue, comprising subjecting the adipose tissue to one or more incubations in an enzymatic digestion solution containing one or more enzymes, and one or more solvent extractions, wherein decellularized adipose tissue comprising an extracellular matrix with well-preserved three-dimensional structure may be obtained. The well-preserved structure may include vascular and/or ductal structures.

The obtained extracellular matrix may include a combination of fibrous and network type collagens. The obtained extracellular matrix may include type IV collagen. The obtained extracellular matrix may include one or more of collagens type I to m, V, and VI. The decellularized adipose tissue may contain elastin and/or elastic fibres.

The decellularized adipose tissue may include laminin, fibronectin, or both. The decellularized adipose tissue may include hyaluronan, chondroitin sulphate, or both. The decellularized adipose tissue may include one or more proteoglycan, glycoprotein, or glycosaminoglycan, or any combination thereof.

The method may include one or more steps involving mechanical disruption. The one or more steps involving mechanical disruption may include one or more freeze-thaw cycles or agitation, or a combination thereof. The one or more freeze-thaw cycles may be carried out in a hypotonic solution, hypertonic solution, or neutral buffer. The method may include one or more rinses in a rinsing buffer. The method may include using at least one polar solvent, at least one non-polar solvent, or a combination thereof.

The method may provide decellularized adipose tissue that is substantially devoid of intact adipose cells. In accordance with an embodiment of the method, subjecting may comprise substantially removing immunogenic components of the adipose tissue.

In one embodiment the method may comprise:
(i) subjecting the adipose tissue to one or more freeze-thaw cycles in a freezing buffer;
(ii) subjecting the adipose tissue to enzymatic digestion;
(iii) subjecting the adipose tissue to one or more polar solvent extractions;
(iv) washing the adipose tissue in rinsing buffer,
(v) subjecting the adipose tissue to enzymatic digestion;
(vi) washing the adipose tissue in rinsing buffer,
(vii) subjecting the adipose tissue to enzymatic digestion;
(viii) washing the adipose tissue in rinsing buffer;
(ix) subjecting the adipose tissue to polar solvent extraction; and
(x) washing the adipose tissue in rinsing buffer.

Also described herein is a method for substantially isolating extracellular matrix material from adipose tissue, comprising subjecting the adipose tissue to one or more incubations in an enzymatic digestion solution and one or more solvent extractions, wherein extracellular matrix material with well-preserved three-dimensional structure may be obtained.

The method may include one or more steps of mechanical disruption, one or more steps of enzymatic digestion, one or more rinses in rinsing buffer, and/or one or more steps of polar solvent extraction. The method may comprise subjecting the adipose tissue to a solvent blend including one or more non-polar solvents and one or more polar solvents.

The method may involve perfusion of the decellularization agents to augment or accelerate the decellularization process, or to facilitate the collection of larger tissue sections, including adipose tissue flaps and/or pedicled adipose flaps with intact feeding arteries and/or veins. Perfusion may involve cannulation of one or more blood vessels in adipose tissue to deliver the decellularization agents via native vasculature of the tissue.

Also described herein is a decellularized adipose tissue comprising an extracellular matrix with well-preserved three-dimensional architecture. The extracellular matrix may include a combination of fibrous and network type collagens. The extracellular matrix may include type IV collagen. The extracellular matrix may include one or more of collagens type I to III, V, and VI. The decellularized adipose tissue may include elastin and/or elastic fibres. The decellularized adipose may include laminin, fibronectin, or both, and/or one or more proteoglycans. The matrix may include hyaluronan, chondroitin sulphate, or both, and/or one or more proteoglycan, glycoprotein, or glycosaminoglycan, or any combination thereof. The decellularized adipose tissue may be prepared according to the methods described herein.

The decellularized adipose tissue may be substantially devoid of intact adipose cells. The decellularized adipose tissue may be substantially free of immunogenic components.

Also described herein is a bioscaffold prepared from the decellularized adipose tissue described herein. The bioscaffold may be used in a surgical procedure, such as plastic and reconstructive surgery, general surgery, cardiac surgery, orthopaedic surgery, neurosurgery, urology, gynecology, or cosmetic surgery. The bioscaffold may be used as a hemostatic agent or as a wound healing dressing. The bioscaffold may be autologous, allogenic, or xenogenic.

A composite bioscaffold incorporating one or more phases in addition to the decellularized adipose tissue may be fabricated. The composite approach may be used to fabricate scaffolds incorporating decellularized adipose tissue with defined scaffold geometries and/or with specific mechanical properties, or to mediate the biodegradation of the decellularized adipose tissue. The composite bioscaffold may incorporate a naturally-derived hydrogel or scaffold component, such as another decellularized scaffold or a derivative of collagen, gelatin, hyaluronan, chondroitin sulphate, chitosan, alginate, silk, fibrin, protein, proteoglycan, glycosaminoglycan, or polysaccharide, in addition to the decellularized adipose tissue. The composite may also include synthetic components, such as poly(ethylene glycol) (PEG)-, polyethylene-, polyurethane-, polylactic acid (PLA)-, polyglycolic acid (PGA)-, polylactic co-glycolic acid (PLGA)-based hydrogels or scaffolds, or synthetic polymers incorporating one or more types of monomer, in addition to the decellularized adipose tissue. The synthetic scaffold may be biodegradable. The composite scaffolds may be subjected to chemical and/or photochemical cross-linking processes to stabilize their structure.

Also described herein is a cell culture substrate prepared from decellularized adipose tissue. The substrate may be used to facilitate attachment of adherent primary cells or cell lines. The cell-seeded decellularized adipose tissue may be cultured in vitro under static conditions or within a bioreactor system, such as a perfusion bioreactor. The decellularized adipose tissue, with or without seeded cells, may also be implanted in vivo in a temporary site, such as within the subcutaneous space or abdominal space, including the omentum, mesentery, or peritoneum. The purpose of the scaffold culture may be cell expansion, cell differentiation, tissue growth, or the production of one or more specific proteins of interest.

Also described herein are particles prepared from the decellularized adipose tissue.

Also described herein is a coating prepared from the decellularized adipose tissue described herein.

Also described herein is a microcarrier bead prepared from the decellularized adipose tissue described herein. The microcarrier bead may include a coating as described herein.

BRIEF DESCRIPTION OF THE DRAWINGS

For a better understanding of the invention, and to show more clearly how it may be carried into effect, embodiments will be described, by way of example, with reference to the drawings, wherein:

FIG. 2A shows a region where the collagen fibres are arranged in parallel in organized bundles. FIG. 2B shows a network-rich region of interwoven collagen fibres, consistent with basement membrane-type architecture.

FIG. 9B shows images of the explanted ASC-seeded DAT scaffolds at 4 days (top) and 14 days (bottom), with visible blood vessels on the surface of the implants. FIG. 9C shows a representative H&E image of an unseeded DAT scaffold at 14 days (R=rat tissue; C=fibrous capsule; D=DAT scaffold; bar=100 μm) showing macroscopic preservation of the implant volume. FIG. 9D shows a representative SEM photomicrograph of an unseeded DAT scaffold (D) at 14 days post-implantation (bar=500 μm), showing a relatively thin fibrous capsule (C) and good integration with the host tissues (R). H&E staining of the central regions of the unseeded DAT (FIG. 9E) and ASC-seeded DAT (FIG. 9F) at 14 days showed cellular infiltration, with a higher degree of cellularity in the ASC-seeded DAT scaffolds (bars=20 μm).

DETAILED DESCRIPTION OF EMBODIMENTS

Figure 1A:
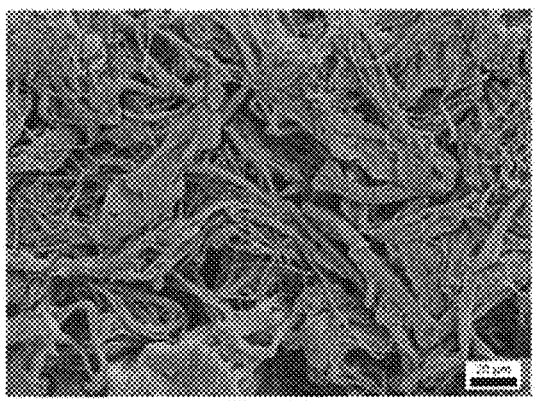
FIGS. 1A to 1D are SEM photomicrographs of decellularized adipose tissue (DAT) obtained as described herein showing (FIG. 1A) ultrastructure of the processed matrix and confirming cellular extraction, (FIG. 1B) regions of network-type collagen, consistent with the rich basement membrane component in adipose tissue, (FIG. 1C) preservation of the macroscopic 3-D architecture of the collagen fibres, and (FIG. 1D) preservation of organized, nanofibrous collagen.

Decellularization of placenta, cartilage, and bone has been investigated in combination with mesenchymal stem cells for adipogenic, chondrogenic, and osteogenic applications, respectively [5-7]. Tissue decellularization typically involves a combination of physical, chemical, and biological treatments that contribute to the removal of the cellular material and the collection of the extracellular matrix (ECM). The efficacy of the decellularization process depends on the nature of the tissues, the length of treatment, and the specific techniques employed. While a number of different decellularization approaches have been described for other tissues, to date, there have been no methods developed to facilitate the collection of matrix material with well-preserved three-dimensional (3-D) structure from adipose tissue (fat).

Adipose tissue is a rich source of ECM, in particular basement membrane (the thin layer of extracellular matrix that underlies epithelial and endothelial cells, and functions to anchor these cells within tissues), useful for adipose tissue regeneration strategies. ECM contains collagen, as well as other components, such as elastic fibres, laminin and fibronectin. A source of intact basement membrane is of particular interest in tissue engineering, as this structure plays a vital role during both organogenesis and wound healing. Techniques have been developed to extract collagen from fat, in order to utilize the matrix as either an injectable cell delivery vehicle, or as a 3-D porous scaffold for larger-volume augmentation [8, 9]. However, no methodology has been described that facilitates the collection of intact ECM, with well-preserved 3-D architecture, from adipose tissue. While the matrix composition is an important factor in mediating the cellular response, the organization of the 3-D architecture is equally significant.

Described herein is a method for decellularizing adipose tissue while substantially preserving the 3-D structure or architecture of the ECM. The adipose tissue may be from mammals, such as, but not limited to humans, cows, sheep, and pigs, or from other animals. The terms "structure" and "architecture" are used interchangeably herein. The method provides decellularized adipose tissue (DAT) including the ECM. The ECM includes collagen. The ECM may include a combination of fibrous and network type collagens. The ECM may include type IV collagen. The ECM may include one or more of collagens type I to II, V, and VI. The DAT may include one or more other proteins, such as laminin or fibronectin. The laminin may be associated with network-type collagen. The DAT may also include one or more growth factor. The DAT may include proteoglycans, glycoproteins, and/or glycosaminoglycans. The DAT may include hyaluronan and/or chondroitin sulphate. The DAT may include elastic fibres or elastin. The DAT may include some cellular fragments, but is substantially devoid of intact cells. The method has been applied to adipose tissue blocks of up to 25 g, as well as lipoaspirates, and the method may be readily adapted for processing larger tissue sections. Perfusion of the decellularization agents may be used, potentially to expedite or augment decellularization, or to facilitate the decellularization of larger tissue sections. The perfusion may be via the vasculature within the adipose tissue and may involve the cannulation of a vessel, such as an artery or vein, within isolated adipose tissue. As described herein, decellularized adipose tissue is source of collagen that has broad applicability in fields such as, for example, plastic surgery and reconstructive surgery, orthopaedics, cardiovascular applications, general surgery, urology, gynecology and neurosurgery, such as for dural repair, and as a hemostatic agent (blood clot inducing material) or wound healing barrier, such as for the treatment of burns or diabetic ulcers.

Also described herein is a method for substantially isolating ECM with well-preserved 3-D structure from adipose tissue. The term "well-preserved 3-D structure" means that the isolated ECM has a 3-D structure that includes a highly-organized combination of fibrous and network type collagens that is similar to the 3-D structure of the ECM in intact adipose tissue. As such, the well-preserved 3-D structure of the isolated ECM promotes, or does not interfere with, normal cellular organization and behaviour of cells in culture, by replicating the cellular microenvironment found in the body, and thereby supporting natural cellular processes, such as cell growth and proliferation. Substantially isolated ECM may include type IV collagen. Substantially isolated ECM may include one or more of collagens type I to III, V, and VI. Substantially isolated ECM may include one or more other proteins, such as laminin or fibronectin. The laminin may be associated with network-type collagen. Substantially isolated ECM may include one or more growth factors. Substantially isolated ECM may include proteoglycans, glycoproteins and/or glycosaminoglycans. Substantially isolated ECM may include hyaluronan and/or chondroitin sulphate. Substantially isolated ECM may include elastic fibres or elastin. Substantially isolated ECM may include decellularized blood vessels with preserved 3-D structure of the conduits, such as arteries and veins. Substantially isolated ECM may include decellularized ductal structures, e.g., if the adipose tissue is taken from the breast. Substantially isolated ECM may include components of the adipose tissue such as proteins and cell fragments, but is substantially devoid of intact adipose cells, whether viable or non-viable. In certain embodiments the isolated ECM is substantially free of immunogenic components, including lysed cells and similar cell debris. By "substantially free of immunogenic components" is meant that such components are at a level insufficient to generate an immune response in a subject into which the material is introduced.

DAT may be used to fabricate a naturally-derived bioscaffold for soft tissue augmentation. DAT may be used as a bulking material for cosmetic and reconstructive applications, such as, for example, a soft tissue filler in cosmetic plastic surgery involving, e.g., the face, including the correction of wrinkles or other minor defects, as well as lip augmentation. DAT may also be used in reconstructive applications and wound healing, such as the repair of congenital birth defects, in the treatment of burns and diabetic ulcers, for the repair of traumatic injuries affecting the soft tissues, or in soft tissue reconstruction following tumour resection. A DAT bioscaffold may be used in general surgical procedures and specific surgical procedures such as cardiac surgery, orthopaedic surgery, neurosurgery, urology, gynecology, or cosmetic surgery. The bioscaffold may be used as a hemostatic agent or as a wound healing dressing. The bioscaffold may be autologous, allogenic, or xenogenic.

For example, DAT may be used as a bulking agent for urological or gynaecological applications, e.g., to help prevent incontinence. In addition, DAT may be employed in orthopaedic applications. For example, DAT may be used to augment the soft tissues in the feet of elderly patients suffering from atrophy, to improve cushioning, and consequently mobility, or DAT may be used for ligament repair. DAT may be employed in neurosurgery, such as for use in the repair of the dura or as a bridging material for repairing gaps in peripheral nerves. DAT may be used in cardiovascular applications. For example, DAT may be used as a carrier of cells or growth factors for the treatment of cardiac or peripheral ischemia. DAT may be used as a hemostatic agent for both non-surgical and surgical (open and endoscopic surgeries) applications.

Most cosmetic soft tissue augmentation strategies to date involve the augmentation of the dermal layer. While this can act as a temporary corrective measure, soft tissue defects in the face are generally caused by changes in the subcutaneous adipose tissue layer that underlies the denrmis. As humans age, the sub-dermal fat layer tends to atrophy in some regions of the face, causing the reticular dermis to attach to the underlying muscle tissue. Repeated contractions of the muscle exert forces on the skin, resulting in fibrosis and the formation of deep wrinkles. Augmentation using substantially isolated ECM as described herein DAT will act to restore the underlying adipose tissue layer to its original state, and will be more effective than a treatment that merely augments the dermis. As the ECM architecture and composition has been shown to dramatically impact cellular behaviour, using fat as the matrix source may promote long-term soft tissue regeneration. It is expected that ECM derived from adipose tissue will provide an ideal environment for adipogenesis.

DAT may be used as a bioscaffold to support cellular attachment. For adipose-based applications, DAT scaffolds can support the adipogenic differentiation of seeded mesenchymal stem cells or other adipose progenitors. A bioscaffold prepared from DAT for soft tissue regeneration may have mechanical properties that allow the scaffold to mimic the native soft tissues into which it is incorporated. This ensures that the implant has a natural feel, and minimizes inflammation and scar tissue formation. At the same time, the bioscaffold stiffness may appropriately influence the differentiation response of seeded stem cells, such as mesenchymal stem cells. A DAT bioscaffold, for adipose tissue engineering applications, may be soft, flexible, and elastic, with a Young's modulus similar to or the same as that of normal fat, i.e., in the range of about 3-4 kPa [10]. The bioscaffold may have sufficient mechanical integrity to withstand post-implantation forces exerted on the tissues, so as to avoid structural collapse of the scaffold, which may be devastating for adipose regeneration. A DAT bioscaffold may degrade at a rate that supports the development of new mature adipose tissue, including differentiated cells from the seeded scaffold and/or infiltrating populations from the host tissues.

A composite DAT-based scaffold incorporating one or more biomaterials in addition to the decellularized adipose tissue may be fabricated for use as a bioscaffold. The composite bioscaffold may include one or more naturally-derived and/or synthetic biomaterials. The composite bioscaffold may include one or more other decellularized scaffold, including, but not limited to, demineralized bone matrix, decellularized bone, decellularized blood vessels, decellularized cartilage, decellularized placenta, decellularized heart valves, decellularized ligament, decellularized dermis, decellularized myocardium, decellularized pericardium, decellularized smooth muscle, decellularized intestine, decellularized mucosa, or decellularized nerve. The composite bioscaffold may incorporate DAT-based microcarriers or particles in addition to the intact DAT. The composite bioscaffold may incorporate derivatives of collagen, gelatin, hyaluronan, chondroitin sulphate, chitosan, alginate, silk, or fibrin, amongst other naturally-derived biomaterials, including protein, polysaccharide, proteoglycan, or glycosaminoglycan, in addition to the decellularized adipose tissue. The composite may incorporate polycaprolactone (PCL)-, polyester-, polyurethane-, poly(ethylene glycol) (PEG)-, polylactic acid/polylactide (PLA)-, polyglycolic acid/polyglycolide (PGA)-, polylactic co-glycolic acid (PLGA)-based hydrogels or scaffolds, amongst other synthetic biomaterials, in addition to the decellularized adipose tissue. The composite bioscaffolds may be subjected to thermal, chemical, enzymatic, and/or photochemical cross-linking processes to stabilize their structure. The purpose of fabricating the composite bioscaffold may be to create a well-defined 3-D architecture and/or shape. The purpose of fabricating the composite bioscaffold may be to tune the mechanical properties and/or biodegradation of the bioscaffold.

A DAT bioscaffold or a composite DAT bioscaffold may include one or more other materials such as, but not limited to, a pharmaceutical agent (e.g., an anti-inflammatory agent, an analgesic agent), a hormone, a growth factor, a protein or peptide, an angiogenic factor, an agent that induces localized cell differentiation or an agent that induces adipogenesis (such as an insulin-sensitizing agent), such as, for example, a thiazolidinedione (e.g., rosiglitazone, troglitazone, pioglitazone), an agent that inhibits degradation of cAMP, such as isobutylmethylxanthine, or an agent that promotes bone mineralization, such as beta-glycerophosphate, ascorbic acid.

A DAT bioscaffold may be seeded with human or animal-derived primary cells or cell lines, including cells that have the capacity to differentiate into mature cells, such as, but not limited to, adipose-derived stem cells, bone marrow derived mesenchymal stem cells, embryonic stem cells, induced pluripotent stem cells, adipocytes, adipoblasts, pre-adipocytes, blood cells, cardiomyocytes, cardiac stem cells, chondrocytes, osteocytes, myocytes, endothelial cells, endothelial progenitor cells, epithelial cells, fibroblasts, hematopoietic stem cells, pericytes, neurons, neural stem cells, neural crest cells, and glial cells, and the cellular response may be probed in vitro and/or in vivo. For example, adipose-derived stem cells (ASC) are a suitable cell source for a range of regenerative strategies, including adipose tissue engineering. Fat is an abundant and accessible source of cells with multilineage differentiation capacity. ASC can differentiate into mature adipocytes and secrete factors in vivo that contribute to regeneration by triggering the migration of host stem cells to the site of implantation, as well as promote vascularization, which is essential for long-term fat stability. ASC may also modulate the immune response, and thus may be utilized as either an autologous or allogenic cell source.

A DAT bioscaffold or a composite bioscaffold incorporating DAT may be used as a cell culture substrate, such as for the culture of adherent cells, including primary cells and cell lines. A cell-seeded DAT-based bioscaffold may be cultured in vitro under static conditions or within a bioreactor system, such as a scaffold-based perfusion bioreactor system. The decellularized adipose tissue, with or without seeded cells, may also be implanted in vivo in a site within the subcutaneous space or abdominal space, including, for example, the omentum, mesentery, or peritoneum. Such implantation may be temporary. The use of DAT as a cell culture substrate may be for the expansion of specific cells of interest, for cell differentiation, or may be for the production of bioproducts, such as tissue or one or more proteins. In one example, a DAT bioscaffold may be used to facilitate the large-scale expansion of cells, such as human ASC, from small biopsy samples to obtain clinically-relevant yields of stem cells that could be applied autologously or allogenically. The cells may be extracted from the DAT scaffold at the end of culture, such as by treatment with an enzyme such as collagenase or trypsin. Alternatively, the cells may be applied therapeutically as, for example, in combination with the DAT as a bioscaffold.

Figure 5:
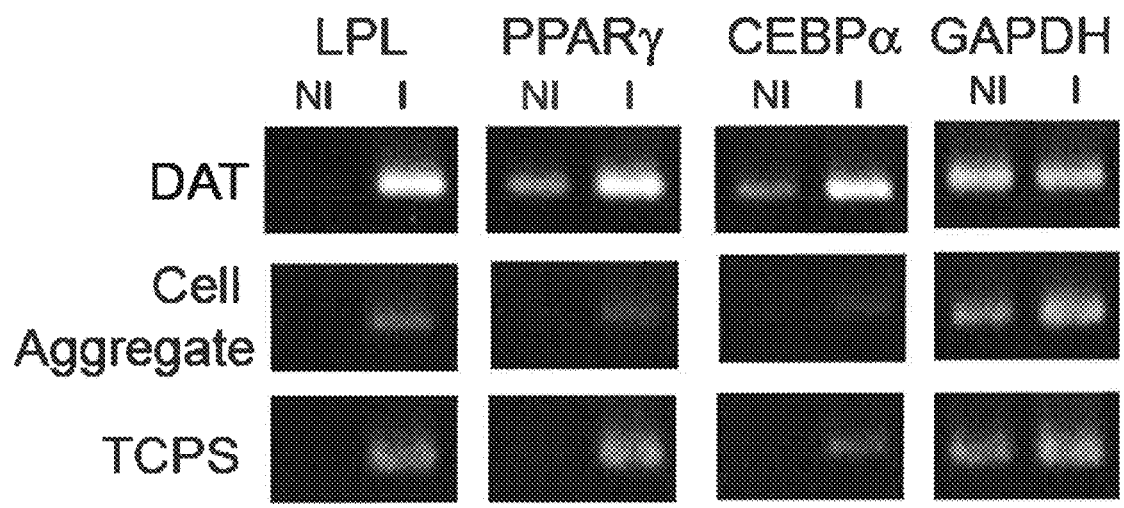
FIG. 5 shows results of an end point RT-PCR study examining the expression of the adipogenic markers lipoprotein lipase (LPL), peroxisome proliferator activated receptor γ (PPARγ), and CCAAT-enhancer binding protein α (CEBPα), with glyceraldhehyde-3-phosphate dehydrogenase (GAPDH) as the housekeeping (i.e., constitutively expressed) gene, in adipose-derived stem cell (ASC)-seeded scaffolds and controls. NI=not induced (cultured in proliferation medium for 10 days). I=induced (cultured in proliferation medium for 72 h, followed by adipogenic differentiation medium for 7 days). CA=cell aggregate culture, where the ASC were cultured in a 3-D sheet format on Millicell™ filter units without exogenous matrix. TCPS=tissue culture polystyrene. The highest relative levels of gene expression were detected in induced DAT scaffolds. The master regulators of adipogenesis, PPARγ, and CEBPα, were expressed in the non-induced DAT scaffolds, indicating that this microenvironment was conducive to adipogenesis without the need for exogenous growth factors. The staining patterns shown are representative of all samples examined (n=3, N=3).

To demonstrate the use of DAT as a regenerative scaffold for adipose tissue engineering, the in vitro adipogenic response of seeded human ASC was probed. The results highlight the importance of the 3-D microenvironment on cellular behaviour. Moreover, the substantially intact decellularized adipose tissue ECM appears to be a permissive environment for fat formation, inducing the expression of adipogenic markers (i.e., genes) without the need for exogenous differentiation factors, as shown in FIG. 5. As such, the embodiments described herein are suitable for large-volume soft tissue augmentation.

An objective of tissue decellularization as described herein is to remove cellular components that would initiate an immune response, while substantially preserving the native structure and composition of the ECM. Tissue decellularization as described herein is detergent-free, which is beneficial due to concerns associated with cytotoxicity and the presence of residual detergents. In one embodiment, the method includes subjecting adipose tissue to one or more incubations in an enzymatic digestion solution (containing one or more enzymes), and one or more polar solvent extractions. In another embodiment, the method includes subjecting adipose tissue to one or more steps involving mechanical disruption, one or more incubations in an enzymatic digestion solution, and one or more polar solvent extractions. In another embodiment, the method includes subjecting adipose tissue to one or more steps involving mechanical disruption, one or more incubations in an enzymatic digestion solution, one or more polar solvent extractions, and one or more rinses in a rinsing buffer. The various steps of the method may be carried out in any order. The duration of each step may be adjusted as required or as may be convenient. For example, enzymatic digestion may be carried out over a period of one or more hours, or overnight. Mechanical disruption includes a procedure that does not substantially damage the ECM. For example, mechanical disruption may include one or more freeze-thaw cycles or one or more steps involving agitation, or a combination thereof. Agitation may include physical agitation of the adipose tissue and/or stirring or flowing a solvent or solution in which the tissue is immersed. A freezing buffer may be employed in the freeze-thaw cycle.

For example, a generalized embodiment including mechanical disruption is shown in Table 1. Enzymatic digestion and polar solvent extraction steps may each be followed by rinsing in buffer solution, and these steps may be repeated as required.

TABLE 1

An example of a generalized method for decellularization of adipose tissue.

| Step | Processing Stages |
|---|---|
| 1 | Mechanical disruption. |
| 2 | Incubate in Enzymatic Digestion Solution. |
| 3 | Polar Solvent Extraction. |
| 4 | Wash in Rinsing Buffer |

In various embodiments, the mechanical disruption, enzymatic digestion, polar solvent extraction, and rinsing buffer steps may each be carried out once, or more than once. For example, the enzymatic digestion may be carried out two or three times, as shown in the embodiments of Tables 2 and 3. As another example, the polar solvent extraction may be carried out twice as shown in the embodiments of Tables 2 and 3, or three or more times. As another example, the rinsing buffer step may be carried out two, three, or four times, as shown in the embodiments of Tables 2 and 3, or more times. The rinsing buffer step may be carried out as many times or for as long as required to substantially remove the activity of a prior step of enzymatic digestion or polar solvent extraction.

TABLE 2

An example of a method for decellularization of adipose tissue.

| Step | Processing Stages |
|---|---|
| 1 | Freeze-thaw in Freezing Buffer. |
| 2 | Incubate in Enzymatic Digestion Solution. |
| 3 | Polar Solvent Extraction. |
| 4 | Wash in Rinsing Buffer. |
| 5 | Incubate in Enzymatic Digestion Solution. |
| 6 | Wash in Rinsing Buffer. |
| 7 | Incubate in Enzymatic Digestion Solution. |
| 8 | Wash in Rinsing Buffer. |
| 9 | Polar Solvent Extraction. |
| 10 | Wash in Rinsing Buffer. |

In another embodiment, shown in Table 3, different enzymatic digestion solutions are used and the method is carried out over five days.

TABLE 3

An example of a method for decellularization of adipose tissue.

| Day | Processing Stages |
|---|---|
| 1 | Freeze-thaw 3 times in Freezing Buffer. |
|   | Incubate overnight in Enzymatic Digestion Solution #1. |
| 2 | Polar Solvent Extraction. |
| 3 | Polar Solvent Extraction. |
| 4 | Wash 3 times in Rinsing Buffer (30 minutes each). |
|   | Incubate for 6 hours in Enzymatic Digestion Solution #1. |
|   | Wash 3 times in Rinsing Buffer (30 minutes each). |
|   | Incubate overnight in Enzymatic Digestion Solution #2. |
| 5 | Wash 3 times in Rinsing Buffer (30 minutes each). |
|   | Polar Solvent Extraction. |
|   | Wash 3 times in Rinsing Buffer (30 minutes each). |

The freezing buffer may be hypotonic or hypertonic, and may include one or more ion chelator such as ethylenediaminetetraacetic acid (EDTA) or ethyleneglycoltetraacetic acid (EGTA) to inhibit the activity of certain enzymes derived from the adipose tissue. An example is 10 mM Tris base and 5 mM EDTA, at, e.g., pH 8.0. Tris-HCl may be used in place of Tris base. Other hypotonic or hypertonic solution formulations may include a solution of water with one or more salts, such as NaCl or KCl, or a hypotonic phosphate buffer. The pH of the hypotonic solution is typically 8.0, but may range between pH 7.0-pH 9.0.

The enzymatic digestion solutions may include one or more proteases effective at breaking cell-matrix interactions, with minimal or no alterations to the ECM. An example of a suitable protease is trypsin, although others may be acceptable, such as, for example, subtilisin from certain bacterial strains. The enzymatic digestion solutions may include one or more other degradative enzymes such as, but not limited to, DNase, RNase, lipase, and/or phospholipase. That is, enzymes that degrade macromolecules are useful in the methods. Optionally, a chelating agent such as EDTA and/or one or more salt may be included in the digestion solutions. For example, enzymatic digestion solution #1 may include 0.25% trypsin and 0.1% EDTA. Additional enzymes in this solution may include DNase, RNase, lipase, and/or phospholipase. An example of enzymatic digestion solution #2 includes 55 mM $Na_2HPO_4$, 17 mM $KH_2PO_4$, 4.9 mM $MgSO_4 \cdot 7H_2O$, 15,000 U DNase Type II, 12.5 mg RNase type III A, and 2000 units lipase type VI-S. Enzymatic digestion solution #2 may also include trypsin/EDTA and/or phospholipase, as well as any combination of DNase, RNase, and/or lipase from various sources.

An example of the polar solvent includes 99.9% isopropanol. Other polar solvents, including, but not limited to, ethanol, methanol, butanol, n-propanol, pentanol, hexanol, isoamyl alcohol, water, acetic acid, formic acid, chloroform, 2,2-dimethoxypropane, dichloromethane, tetrahydrofuran, acetonitrile, methyl ethyl ketone, methyl propyl ketone, dimethyl sulfoxide, dimethylformamide, isopropyl ether, ethyl acetate or blends of solvents, including non-polar components such as n-hexane, isohexane, or diethyl ether may be utilized. It is preferable to avoid use of highly toxic or potentially carcinogenic or mutagenic solvents, such as benzene or toluene, due to safety concerns associated with such solvents.

The rinsing buffer may include water containing one or more salts, at a substantially neutral pH. An example of the rinsing buffer includes 8 g/L NaCl, 200 mg/L KCl, 1 g/L $Na_2HPO_4$, and 200 mg/L $KH_2PO_4$ at pH 7.4. An alternative rinsing buffer is phosphate buffered saline (without $Ca^{2+}$ or $Mg^{2+}$) at pH 7.4. Another example of a rinsing buffer is Hanks Buffered Salt Solution supplemented with 10 mM HEPES at pH 7.4.

Processing may be conducted under agitation at 37° C. The solutions may be supplemented with antibiotics and/or antimycotics, as well as protease inhibitors.

The embodiment of Table 3 has been optimized to minimize processing time and solution requirements. It is a cost-effective method and is expected to be scalable. However, the method may be adjusted or further optimized as may be required for specific applications. For example, enzymatic digestion solution #1 and #2 may be the same or different. Each step involving polar solvent extraction may use the same or different solvent solution, and may include a blend of polar and non-polar solvents. Similarly, each step involving a rinsing buffer may use the same or different rinsing buffer.

Adipose tissue may be obtained from patients undergoing elective surgery, e.g., involving the abdomen or breast. However, any available fat source may be processed (i.e., from other tissue sites), including the omentum or visceral fat, or adipose tissue of the extremities including the face, arms, legs and feet. The embodiment of Table 3 has been used with excised tissue blocks, and may be adapted to process larger tissue blocks, for example, by including additional stages of enzymatic digestion and solvent extraction. The embodiment may also be adapted to include the perfusion of the decellularization agents into the tissues. The perfusion may involve the cannulation of one or more blood vessels in an adipose tissue pedicle or flap. Such an embodiment may be used with lipoaspirates obtained from liposuction procedures. For lipoaspirate samples, filters may be incorporated to facilitate the sample collection and solution changing procedures. As an alternative, the lipoaspirated materials may be centrifuged during processing to collect the DAT in the pellet, with the supernatants being substantially the various solutions described above.

The use of adipose tissue as a source of ECM as described herein exploits the fact that fat is a uniquely expendable material, and is abundant and available. Moreover, for adipose tissue augmentation applications, use of matrix specifically derived from the tissue that plastic surgeons are trying to augment/regenerate, in accordance with the embodiments described herein, is a unique approach (i.e., using fat, rather than dermal sources, for volume augmentation). Adipose tissue is a particularly rich source of basement membrane components, including collagen type IV and laminin, and it is well recognized that the basement membrane plays a critical role in tissue and organ morphogenesis and wound healing. DAT may also contain elastic fibres and/or elastin, and intact decellularized vascular structures, such as blood vessels. DAT from the breast may contain decellularized ductal structures. DAT may contain one or more growth factors. DAT may be used as either an autologous or allogenic scaffold.

The methods described herein may be applied to adipose tissue from human and non-human subjects. Tissue augmentation and surgical procedures using DAT and ECM as described herein may be applied to human and non-human subjects. Adipose tissue from animal sources including, but not limited to, bovine or porcine fat, may also be processed for use as a xenogenic scaffold in humans. The methods for decellularizing adipose tissue described herein substantially remove immunogenic components of the tissue and accordingly are suitable for preparation of xenogenic materials. However, human adipose tissue is frequently disposed of as medical waste, and represents a rich source of readily-available human collagens, while at the same time, the procedure avoids any concerns about xenogenic disease transmission. Discarded fat may be collected and stored in freezers prior to processing. Freezing is not a problem, as freezing may be the first step in the decellularizing procedure. Liposuction may be used to obtain smaller amounts of adipose tissue, which may be useful for autologous or allogenic tissue augmentation, such as cosmetic applications. It is expected that DAT may be stored stably for years as an off-the-shelf biomaterial.

Alternative decellularization approaches were investigated, including protocols involving the non-ionic detergent Triton-X100, and the anionic detergents lauroyl sarcosinate, sodium dodecyl sulphate (SDS), and sodium deoxycholate. All of these detergents have been implemented with varying degrees of success in the decellularization of other types of tissues [11]. Recently, three other groups have reported on studies related to the decellularization of adipose tissue or lipoaspirated fat with protocols that vary substantially from those described herein, and primarily rely on detergent-based methods [12-14]. The use of detergents raises concerns with safety, due to the potential for the presence of residual cytotoxic chemicals in the processed matrix. In particular, SDS has been shown to strongly interact with ECM components, altering the matrix architecture [15]. Other detergents can also interact with the ECM, potentially causing degradation to the structure. In the studies undertaken, both SDS and sodium deoxycholate caused dramatic swelling of the matrix and irreversible macroscopic degradation of the structure into a gel-like substance. Further, SDS is difficult to remove at the end of processing, and can potentially impact cellular viability and infiltration into the processed matrices [16]. These results suggested that a detergent-free extraction protocol as described herein provides a more clinically-applicable approach. Further, while some of the detergent-based methods showed promise, all required significantly longer processing times than the enzymatic and polar solvent extraction protocol described herein.

The DAT material may be further processed through enzymatic digestion and/or acid solubilization to prepare a coating, or to fabricate microcarriers for use in cell culture and delivery. The DAT material may also be physically processed, such as through cryo-milling, to fabricate particles. While the digestion and solubilization stages will invariably disrupt the preserved 3-D architecture of the ECM, these techniques make use of the DAT as a rich source of purified collagens for scaffold fabrication. As an example, the DAT may be digested in 0.5 M acetic acid solution containing 25 mg pepsin/g of wet weight DAT. Following the completion of digestion, the pepsin may then be inactivated by raising the pH to 8.0 with 10 M NaOH, followed by reducing the pH to less than 3.5 with glacial acetic acid. The digested DAT may be applied to a variety of surfaces as a coating, and allowed to air dry. The coating may be stabilized through the use of a cross-linker, such as, for example, glutaraldehyde, rose bengal, or riboflavin.

Further processing, based on modifications to the methods developed by Tebb et al.[17], allow for the fabrication of porous microcarriers (e.g., beads) from the DAT. In brief, the solubilized DAT may be mixed with a porogen, such as sodium alignate solution (typical concentration in the range of about 3% w/v), and added dropwise through a blunt needle, under the control of a syringe pump, into a stabilizing buffer, such as a solution of calcium chloride. Disruptive airflow and agitation may be used to control the bead diameter. The beads may then be stabilized through chemical cross-linking with a variety of agents, such as, for example, glutaraldehyde, riboflavin, rose bengal, or genipin. Alternatively, the beads may be stabilized through the use of an enzymatic crosslinker, such as transglutaminase. The porogen may then be extracted to yield porous beads. For example, the alginate may be extracted from the beads using a sodium citrate solution, to yield a porous 3-D structure. The microcarrier beads may be effective for large-scale expansion of a variety of cell types including, but not limited to, mesenchymal stem cells, adipose-derived stem cells, osteoblasts, and chondrocytes. The microcarriers may be used to support the differentiation of stem or progenitor cells. The microcarriers may be used as an injectable delivery vehicle for cells or growth factors, or as a bulking agent for small volume augmentation, such as for the correction of small defects and wrinkles in the face.

All cited publications are incorporated herein by reference in their entirety.

Embodiments are further described in the following non-limiting working examples.

WORKING EXAMPLE 1

Materials

All chemicals, unless otherwise stated, were purchased from Sigma-Aldrich Canada Ltd. (Oakville, Canada) and were used as received.

Adipose Tissue Procurement

Excised adipose tissue samples and lipoaspirates were collected from female patients undergoing elective surgery involving the abdomen or breast at the Kingston General Hospital or Hotel Dieu Hospital in Kingston, Canada. The tissues would normally have been discarded as a part of the routine operating procedure. The excised samples were delivered to the lab on ice for processing within 2 hours of extraction, in sterile, cation-free phosphate buffered saline (PBS).

Adipose Tissue Decellularization

A decellularization protocol as detailed in Table 3 was used for excised adipose tissue samples and lipoaspirate materials. Prior to processing, the freshly-isolated excised adipose tissue samples were cut into pieces ranging in mass between 20-25 grams. In the case of lipoaspirates, the volume was selected to yield a mass in the same range. Up to four excised tissue sections were simultaneously processed in a 250 mL plastic tub, containing 100 mL of decellularization solution, at 37° C. under agitation on an Excella™ 24 Benchtop Incubator (New Brunswick Scientific) at 120 RPM. All decellularization solutions were supplemented with 1% antibiotic-antimycotic solution (ABAM) and 1% phenylmethanesulphonylfluoride (PMSF).

The samples were first subjected to three cycles of freeze-thaw (−80° C. to 37° C.) in a freezing buffer, a hypotonic tris buffer (pH 8.0) containing 10 mM Tris base and 5 mM ethylenediaminetetraacetic acid (EDTA). Next, the tissues were transferred into enzymatic digestion solution #1, consisting of 0.25% trypsin/0.1% EDTA (Gibco, Burlington, Canada), and incubated overnight for approximately 16 hours. Subsequently, the samples underwent a 48-hour polar solvent extraction in 99.9% isopropanol, to remove the lipid content. The processed tissues were then rinsed three times (30 minutes) in a rinsing buffer containing 8 g/L NaCl, 200 mg/L KCl, 1 g/L $Na_2HPO_4$, and 200 mg/L $KH_2PO_4$ (pH 8.0), and incubated for 6 hours in Enzymatic Digestion Solution #1. Following an additional three washes in Rinsing Buffer Solution, the samples were transferred into the Enzymatic Digestion Solution #2, containing 55 mM $Na_2HPO_4$, 17 mM $KH_2PO_4$, 4.9 mM $MgSO_4.7H_2O$, 15,000 U DNase Type II (from bovine pancreas), 12.5 mg RNase Type III A (from bovine pancreas), and 2000 Units Lipase Type VI-S (from porcine pancreas), for 16 hours of processing overnight. The next morning, the matrix was rinsed three times (30 min) in Rinsing Buffer Solution and subjected to a final polar solvent extraction in 99.9% isopropanol for 8 hours. At the end of the processing, the DAT was rinsed a final three times (30 min) in Rinsing Buffer Solution, rinsed three times (30 min) in 70% ethanol, and stored in sterile PBS supplemented with 1% ABAM at 4° C.

Histological and Immunohistochemical Characterization

Representative samples of human adipose tissue and DAT were fixed in 10% neutral buffered formalin for 24 hours, rinsed, and sent in sterile PBS to the Pathology Research Lab at the Toronto General Hospital, Toronto, Canada, for histological and immunohistochemical staining. The staining was conducted to confirm the efficacy of the cellular extraction process, as well as to characterize the distribution of the basement membrane components, collagen type IV (CIV) and laminin (LN). All samples were paraffin-embedded and sectioned (6 μm sections). Hematoxylin and eosin (H&E) staining and Masson's Trichrome staining were used to detect the presence of residual cells or cell fragments, and to characterize the collagen structure of the DAT. The immunohistochemical staining to localize human CIV (1:100 dilution, Dako Canada, Clone CIV 22) and LN (pepsin epitope retrieval, 1:100 dilution, Sigma, rabbit polyclonal) involved detection with the streptavidin-ABC (avidin/biotinylated enzyme complex)/horse radish peroxidase (HRP) system with NovaRed™ as the substrate (Vector Laboratories).

Scanning Electron Microscopy (SEM)

SEM was conducted on samples of the DAT at the end of processing to confirm decellularization and to assess the architecture of the matrix. For the analysis, 200 mg samples were fixed in 2.5% glutaraldehyde (SEM grade) for 1 hour at room temperature, and then for 24 hours at 4° C. After extensive rinsing in PBS, the samples were snap frozen in liquid nitrogen, and fractured. A chemical drying procedure was utilized to prepare the samples. In brief, the samples were first dehydrated in an ethanol (EtOH) series, and subsequently dried with hexamethyldisilazane (HDMS) (2:1 100% EtOH:HDMS for 15 min; 1:2 100% EtOH:HDMS for 15 min; 100% HDMS for 15 min, repeated 3 times and air dried overnight). The dried matrices were mounted onto microscopy studs with carbon tape, and sputter-coated in gold. Micrographs (FIGS. 1A-1D, 2A-2B, 3) were obtained with a working distance of 15 mm and an accelerating voltage of 10 kV on a JEOL 840 microscope.

Adipose-derived Stem Cell Culture

Primary cultures of human ASC were established from subcutaneous abdominal adipose tissue samples, according to methods described in the literature [15]. The donor age, weight, and height were recorded. Passage 2 cells were used for the seeding experimentation.

To induce adipogenic differentiation, the cells were cultured in serum-free DMEM:Ham's F-12 supplemented with 15 mM $NaHCO_3$, 15 mM HEPES, 33 μM biotin, 17 μM pantothenate, 10 μg/mL transferrin, 100 nM cortisol, 66 nM insulin, 1 nM triiodothyronine (T3), 100 U/mL penicillin and 0.1 mg/mL streptomycin. For the first 72 h of differentiation, 0.25 mM isobutylmethylxanthine (IBMX) and 1 μg/mL of troglitazone were added to the differentiation medium.

Cell Seeding

To prepare the DAT for the cell seeding experiments, excess buffer was removed by blotting and the processed tissues were cut into 200 mg hydrated scaffolds. The scaffolds were then decontaminated by three 30-minute rinses in 70% ethanol, rehydrated with three 30-minute washes in sterile PBS, and incubated (37° C., 5% $CO_2$) overnight in growth medium. Each DAT scaffold was then transferred into an uncoated Millicell™ filter unit (12 mm diameter, 0.4 μm pore size, Millipore, Billerica, Mass., USA) and seeded with $1 \times 10^6$ ASC (Passage 2) in 200 μL of complete growth medium to promote cell attachment. Each filter was cultured in an individual well of a 6-well plate containing 5 mL of complete growth medium (37° C., 5% $CO_2$). After 24 hours in culture, the DAT scaffolds were removed from the filter units and placed directly in the 6-well plates, to allow for greater exposure to the medium. Samples of the seeded DAT scaffolds were collected at 24 h, and fixed in 10% neutral buffered formalin for 24 hours in preparation for histological and immunohistochemical characterization, as described above.

To better assess the impact of the DAT scaffold on the cellular behaviour in three-dimensions, high-density Cell Aggregate (CA) samples were also prepared, following methods described in the literature [18]. In brief, Millicell™ filter units (12 mm diameter, 0.4 μm pore size) were coated with 0.5 mg/mL of collagen type IV (human placental origin), and seeded with $1 \times 10^6$ ASC (Passage 2) in 500 μL of complete growth medium. The filters were cultured in 6-well plates containing 5 mL/well of complete growth medium (37° C., 5% $CO_2$).

The culture medium was changed every 2 to 3 days. To induce differentiation, after 72 hours, the DAT and CA samples were rinsed three times in sterile PBS, and the complete growth medium was replaced with differentiation medium, described in the previous section. Triplicate tissue culture polystyrene (TCPS) controls (differentiated and non-differentiated) were prepared for all experiments by seeding 6-well plates at 300,000 cells/well in 5 mL of complete growth medium. Adipogenic differentiation was induced as with the DAT and CA samples, at 72 hours in culture after rinsing in PBS. For logistical reasons, tissues from three different donors were used for the gene expression studies (N=3), and cells from another three donors (N=3) were used for the quantification of GPDH enzyme activity. To minimize concerns with cell donor variability, ASC from the same donor were used to seed all DAT, CA, and TCPS samples for all time points in a single trial of each assay.

RT-PCR Analysis

End point RT-PCR was conducted to characterize the gene expression of key adipogenic markers (PPARγ, CEBPα, LPL) and extracellular matrix components (collagen I (CI), collagen II (CII), collagen IV (CIV)) in samples cultured under growth (10 days after seeding) and differentiation medium (10 days after seeding/7 days after the induction of differentiation) conditions (n=3, N=3). Glyceraldehyde-3-phosphate dehydrogenase (GAPDH) and transferrin receptor (TfR) were included as housekeeping genes [19].

Total RNA was isolated using TRIzol® reagent (Invitrogen, Burlington, Canada). Briefly, the DAT scaffolds were flash-frozen in liquid nitrogen and ground with a mortar and pestle. Each scaffold was homogenized in 1 mL of TRIzol® reagent and processed according to the standard methods for tissues. The same RNA extraction procedure was used for the CA and TCPS samples. The concentration and purity of the RNA was measured using a NanoDrop spectrophotometer (ND1000; NanoDrop Products, Wilmington, Del., USA). The 260/280 ratio generally ranged between 1.9 and 2.0. Unseeded DAT scaffolds were included as a negative control in the initial trials, but insufficient RNA was collected to facilitate further analysis.

First-strand cDNA was synthesized from 1 μg of total RNA in a 20 μL reaction volume containing first strand buffer (50 mM Tris-HCl, 75 mM KCl, 3 mM $MgCl_2$), 10 mM dithiothreitol (DTT), 0.09 $OD_{260}$ units of random primers (Invitrogen), 0.5 mM of each dNTP (Invitrogen), and 200 units of SuperScript™ II RT (Invitrogen). Minus-RT controls were prepared for each sample. The gene specific primers (Invitrogen; 50 nM, desalted), shown in Table 4, were designed using Primer3 software. The melting temperature for all of the primer sets was 60° C. To detect genomic contamination, all primers, with the exception of the CEBPα primers, were designed to span intron-exon boundaries. Each PCR reaction was conducted in a 50 μL reaction volume with 2.5 μL of diluted cDNA (containing 50 ng of input RNA), 1×Taq buffer (10 mM Tris-HCl, 50 mM KCl, 0.08% Nonidet P40), 250 nM forward primer, 250 nM reverse primer, 250 nM of each dNTP (Invitrogen), 2.5 mM $MgCl_2$, and 0.375 units of recombinant Taq DNA Polymerase (Fermentas). A Bio-Rad C1000 thermal cycler was used and the PCR conditions were 95° C. for 5 minutes followed by 35 cycles of 30 s at 95° C., 30 s at 58° C., and 1 minute at 72° C. A final extension was conducted for 5 min at 72° C. Minus-RT and no template controls were included in every run. The PCR products were separated by electrophoresis on 5% agarose gels, stained with ethidium bromide, and detected under ultraviolet light (G:Box Chemi HR16; Syngene, Cambridge, UK).

TABLE 4

Gene specific primers used in the PCR study.

| Gene | Accession No. | Description | Primers | Fragment Length (bp) |
|---|---|---|---|---|
| PPARγ | NM_138712 | Human peroxinome proliferative activated receptor gamma | F: TTCAGAAATGCCTTGCAGTG (SEQ ID NO: 1) R: CCAACAGCTTCTCCTTCTCG (SEQ ID NO: 2) | 84 |
| CEBPα | NM_004364 | Human CCAAT-enhancer binding protein alpha | F: CAGAGGGACCGGAGTTATGA (SEQ ID NO: 3) R: TTCACATTGCACAAGGCACT (SEQ ID NO: 4) | 107 |

TABLE 4-continued

Gene specific primers used in the PCR study.

| Gene | Accession No. | Description | Primers | Fragment Length (bp) |
|---|---|---|---|---|
| LPL | NM_000237 | Human lipoprotein lipase | F: GTCCGTGGCTACCTGTCATT (SEQ ID NO: 5)<br>R: TGGCACCCAACTCTCATACA (SEQ ID NO: 6) | 94 |
| COL1A1 | NM_000088 | Human collagen type I, alpha 1 | F: AAGAGGAAGGCCAAGTCGAG (SEQ ID NO: 7)<br>R: CACACGTCTCGGTCATGGTA (SEQ ID NO: 8) | 91 |
| COL2A1 | NM_001844 | Human collagen type II, alpha 1 | F: TCTACCCCAATCCAGCAAAC (SEQ ID NO: 9)<br>R: GTTGGGAGCCAGATTGTCAT (SEQ ID NO: 10) | 137 |
| COL4A1 | NM_001845 | Human collagen type IV, alpha 1 | F: GGTATTCCAGGATGCAATGG (SEQ ID NO: 11)<br>R: GCACATGGCCAAGTATCTCA (SEQ ID NO: 12) | 139 |
| GAPDH | NM_002046 | Human glyceraldehyde-3-phosphate dehydrogenase | F: ACAGTCAGCCGCATCTTCTT (SEQ ID NO: 13)<br>R: ACGACCAAATCCGTTGACTC (SEQ ID NO: 14) | 94 |
| TfR | NM_003234 | Human transferrin receptor | F: AGACTTTGGATCGGTTGGTG (SEQ ID NO: 15)<br>R: TTAAATGCAGGGACGAAAGG (SEQ ID NO: 16) | 62 |

Glycerol-3-Phosphate Dehydrogenase Activity

The cellular GPDH enzyme activity levels (GPDH Assay Kit, KT-010; Kamiya Biomedical Corporation) were characterized at 72 hours and 7 days after the induction of differentiation (n=3, N=3) in the DAT and CA samples, using methods described in the literature [20]. Differentiated and undifferentiated cells on TCPS were included as positive and negative controls respectively. The Bio-Rad protein assay with an albumin standard was used to determine the total cytosolic protein content within each sample, for the purposes of data normalization.

Each DAT and CA sample was processed by mincing in 1 mL of the enzyme extraction reagent provided with the kit (4° C.) and disruption by 3 five-second bursts of sonication with intermittent cooling on ice. The TCPS samples were similarly disrupted with sonication. The cytosolic protein fraction was obtained by centrifuging the samples at 16000×g for 15 minutes at 4° C. All supernatant samples were immediately assayed for GPDH activity and total protein content according to the manufacturers' instructions. The GPDH data is expressed in terms of mUnits/mg total intracellular protein (mU/mg), where 1 unit is defined as the GPDH activity required to oxidize 1 μmole of NADH in 1 minute.

Results

The Decellularization Process

A detergent-free decellularization methodology was established to isolate the collagen-rich extracellular matrix of adipose tissue and liposuction materials. At the end of the 5-day extraction procedure, a significant volume of loose, white matrix was collected. Qualitatively, for the excised samples, the decellularized adipose tissue (DAT) had similar dimensions to the tissue block at the beginning of the processing. More quantitatively, the hydrated mass of the matrix typically represented between 30-45% of the original tissue mass, depending on the specific tissue source. In general, tissues isolated from the breast had a higher fibrous content than those collected from the abdominal region. As a scaffolding material, the DAT could be easily manipulated using forceps, cut into a variety of sizes, and packed into moulds of varying three-dimensional architectures. H&E staining confirmed the absence of cells and cell debris in the matrix at the end of processing. Immunohistochemical staining localized the basement membrane components LN and CIV in the decellularized matrix. In mature human adipose tissue, LN was richly expressed in the basement membrane that separates individual adipocytes, as well as along the lining of the supporting vascular structures. The LN content was conserved during the tissue processing. The staining patterns indicated that there was LN lining the empty lumens of former blood vessels, as well as diffuse staining in the network-rich regions, where the adipocyte fraction had been removed. Consistent with the pre-processing staining results, LN was not expressed in the highly-fibrous regions of the matrix. Similar to LN, CIV was expressed in the basement membrane associated with the mature adipocytes and vasculature. After processing, there were detectable levels of CIV in the network-type regions and lumens, although the intensity of the staining was slightly diminished.

Collagen Architecture

Macroscopically, the architecture of the matrix appeared to be well-preserved following processing. Masson's Trichrome staining confirmed the effectiveness of the decellularization process, indicating that there were no residual cells or cellular debris present in the matrix at the end of processing. In addition, the staining was used to examine the collagen in greater detail. Based on the staining patterns, there were four distinct regions of matrix architecture in the DAT. The first region was comprised of densely-packed collagen fibres arranged to form bundles that imparted the scaffold with significant bulk and mechanical integrity. These regions were derived from the fibrous tissues that define and separate individual fat lobules in adipose tissue. Breast tissue, with its well-defined lobular architecture, tended to have a higher connective tissue content than subcutaneous abdominal fat. Within the fibrous zone, regions containing lumens were identified, each having a well-defined border. Immunohistochemical staining showed that these lumens were lined with LN and CIV. Based on these staining patterns, the lumens represent decellularized vascular structures that were preserved during the processing. The third identifiable region had a cross-woven pattern of fibrous collagen, with void pores. The final region was similarly arranged, but was comprised of a much finer network of collagen fibres, and contained a higher content of CIV.

SEM Analysis

Figure 1B:
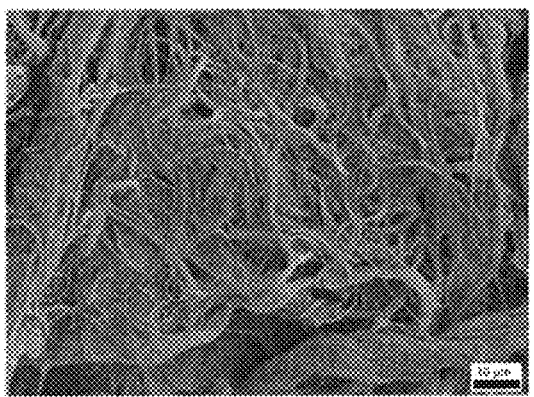
Figure 1C:
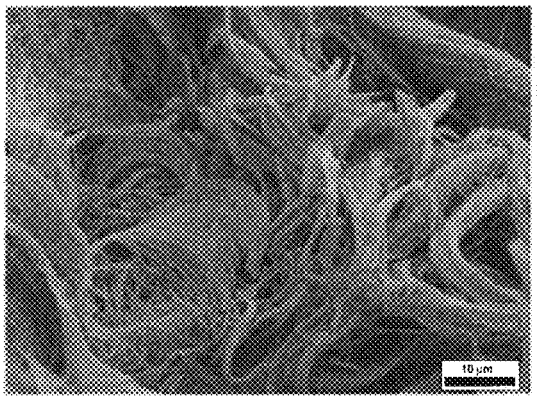
Figure 1D:
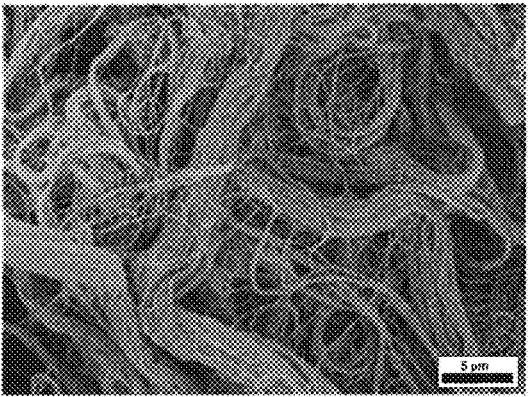
Figure 2A:
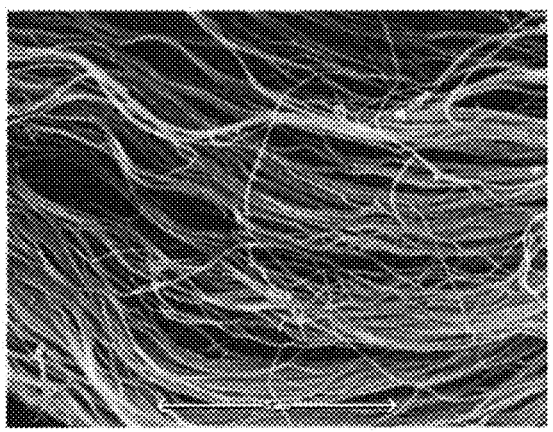
FIGS. 2A and 2B are high magnification SEM photomicrographs of DAT, as described herein. The images show the preservation of fine collagen network architectures of the adipose extracellular matrix, with varying arrangements within the overall tissue structure.
Figure 2B:
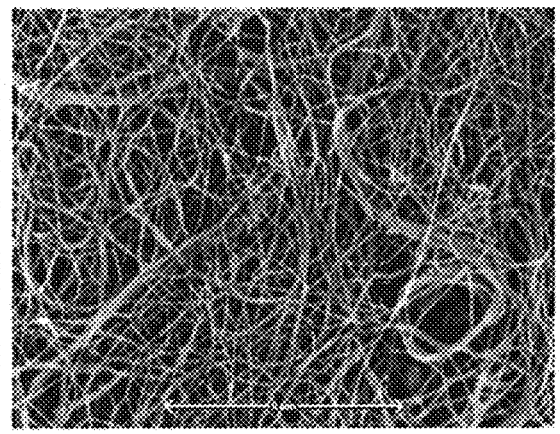
Figure 3:
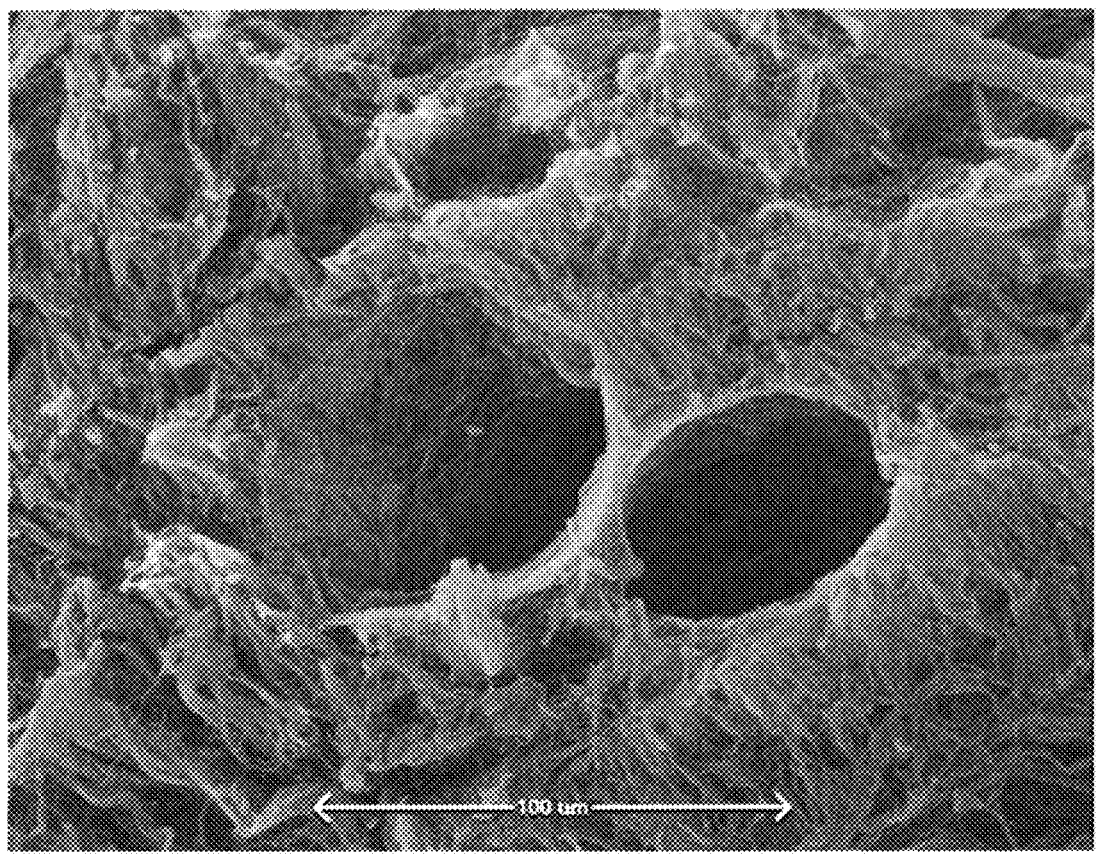
FIG. 3 is an SEM photomicrograph of DAT, as described herein, showing the preservation of the architecture of blood vessels within the matrix at the end of processing. The image shows that the endothelial lining on the lumen of the vessels has been extracted, exposing the network-rich extracellular matrix characteristic of the underlying basement membrane.
Figure 4A:
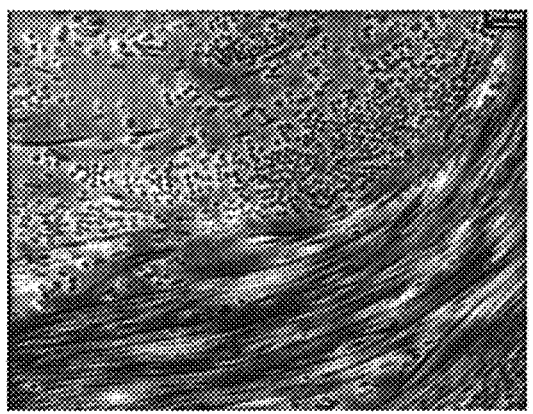
FIGS. 4A to 4D are TEM photomicrographs of DAT obtained as described herein, confirming cell extraction and showing (FIG. 4A) the interwoven nature of the collagen fibres, (FIG. 4B) elastic fibres interspersed within the collagen fibres, (FIG. 4C) the characteristic banding pattern of fibrillar collagen, suggestive of type I collagen, within an aligned region of the fibres of the decellularized adipose tissue, and (FIG. 4D) an end-on view of a region of densely-packed collagen fibres (characteristic of collagen type I) within the matrix. The bars in the top right corner of each panel indicate a distance of 200 nm.
Figure 4B:
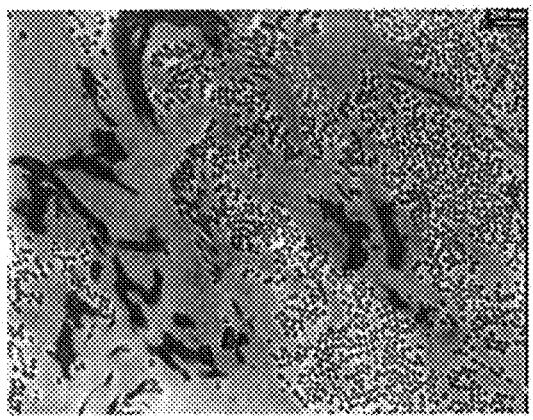
Figure 4C:
Figure 4D:
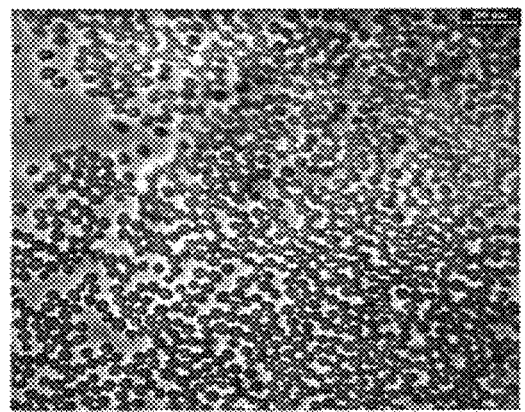

The SEM analysis confirmed the effectiveness of the decellularization protocol, as no cells or cell fragments could be visualized in any regions of the processed matrix (FIGS. 1A-1D). Further, the overall ultrastructure of the ECM appeared to be well-preserved following processing. As with the Masson's Trichrome staining, different regions of matrix architecture could be visualized in the DAT. Thick bundles of fibrous collagen, which would impart mechanical strength, were interconnected with much finer, network-type collagens (FIGS. 1A, 1C). There were regions almost entirely comprised of networks of branching, interwoven collagen, consistent with the high basement membrane content found in adipose tissue (FIG. 1B). Even at high magnification, nano-fibrous collagen architectures were intact, indicating that the developed protocol caused minimal damage to the matrix (FIG. 1D).

Cell Seeding

The DAT scaffolds were seeded in the Millicell™ filter units to maximize cellular attachment to the matrix. Samples sent for histological analysis at 24 h after seeding showed that the ASC were well distributed, and had attached and spread on the scaffolds. The loose nature of the DAT scaffold facilitated cellular infiltration, with cells present in the H&E stained sections taken from the top, middle, and bottom portions of the constructs. There was no evidence of cells in the unseeded control scaffolds. Immunohistochemical staining also revealed that the ASC were expressing the protein LN. Positively stained cells could be readily visualized in the fibrous regions of the DAT scaffolds, previously shown not to contain LN. Similar examination of CIV-stained sections revealed that the ASC were not expressing CIV, with staining patterns consistent with the unseeded controls.

Gene Expression

In the adipogenic gene expression study, no detectable levels of the adipogenic markers LPL, PPARγ, or CEBPα were found when the ASC were cultured in growth medium in either CA culture within the Millicell™ filter units, or in monolayer culture on TCPS (FIG. 5). In contrast, the non-induced DAT scaffolds showed relatively high expression levels of both PPARγ and CEBPα, the master regulators of adipogenic differentiation [21]. After culturing in adipogenic differentiation medium for 7 days, the three adipogenic markers were detected in all of the sample groups. However, the highest levels of expression were consistently associated with the cells seeded on the DAT scaffolds (FIG. 5). The inclusion of TfR as a secondary housekeeping gene (results not shown) confirmed the results shown for GAPDH.

Figure 6:
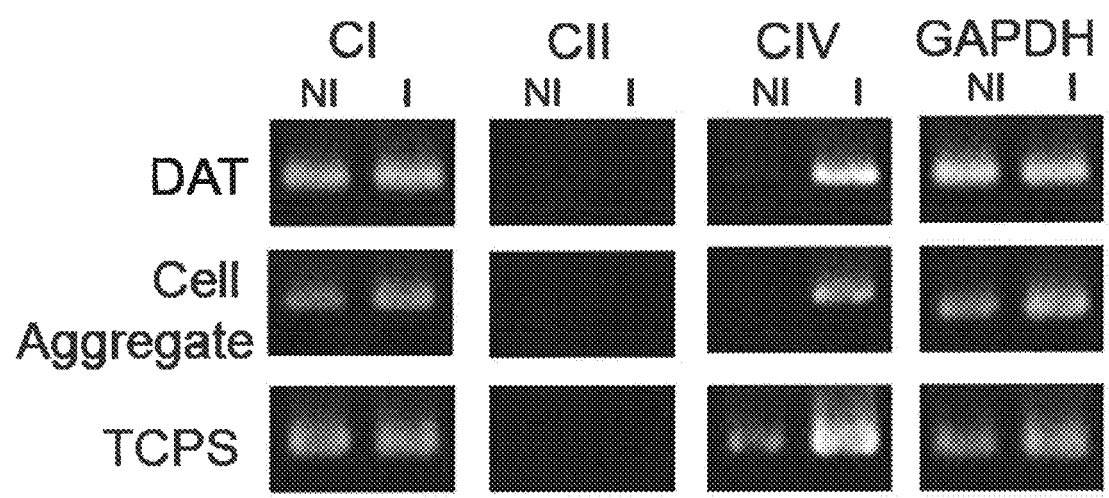
FIG. 6 shows results of an end point RT-PCR analysis of ECM gene expression in ASC-seeded scaffolds and controls. NI=not induced (cultured in proliferation medium for 10 days). I=induced (cultured in proliferation medium for 72 h, followed by adipogenic differentiation medium for 7 days). Collagen type I was expressed in all samples. Collagen type II, commonly associated with the chondrogenic lineage, was not expressed. Collagen type IV was expressed in all of the induced samples, as well as the undifferentiated TCPS control. The staining patterns shown are representative of all samples examined (n=3, N=3).

As the matrix-producing ASC are responsible for the re-organization of the ECM environment during adipogenesis [22, 23], a study was undertaken to examine the expression of three lineage-associated collagens (FIG. 6). Collagen type I was expressed in both the non-induced and induced conditions for the DAT scaffold, CA, and TCPS culture conditions. While collagen type I is frequently linked with the osteogenic lineage, it is also highly expressed in the connective tissue component of fat [24]. Collagen type II, most typically associated with the chondrogenic lineage [25], was not expressed in any of the samples. Consistent with the literature, the basement membrane component collagen type IV was detected in all of the induced samples [26]. Interestingly, collagen type IV was also expressed in the non-induced ASC grown on TCPS (FIG. 6). In contrast, only very low levels of expression were found in the non-induced DAT scaffold group (consistent with the CIV immunostaining results), and the gene was virtually undetectable in the non-induced CA samples.

Enzyme Activity

Figure 7:
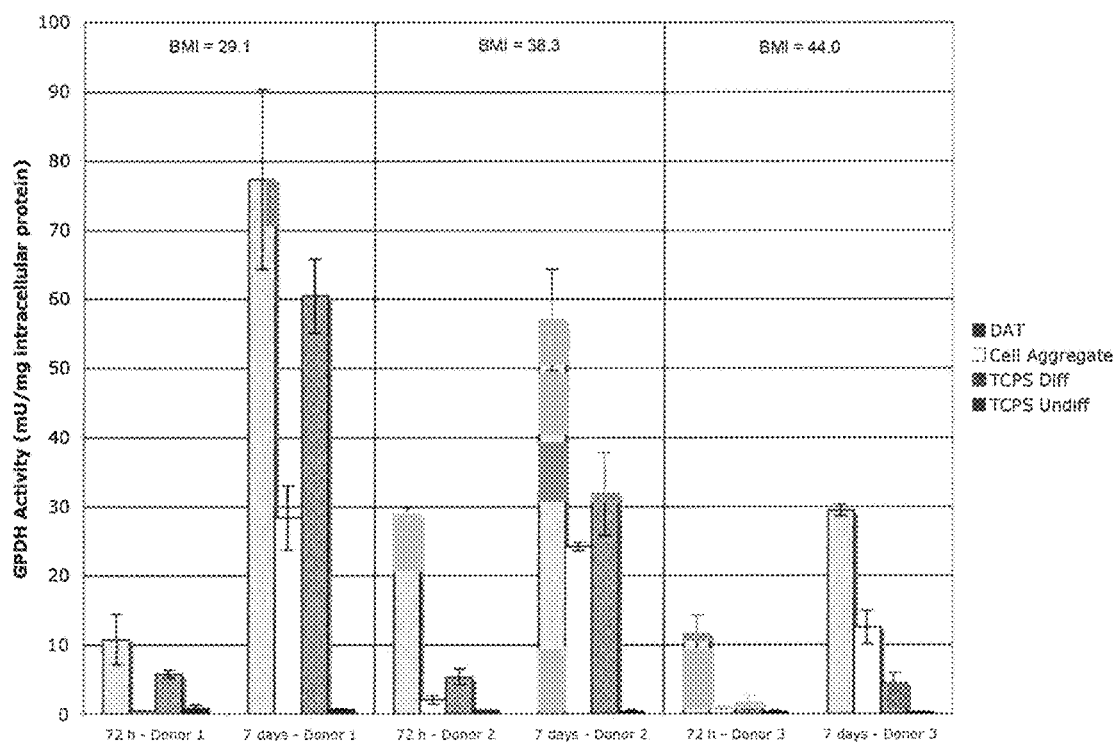
FIG. 7 is a bar chart showing mean glycerol-3-phosphate dehydrogenase (GPDH) enzyme activity normalized to the total intracellular protein content per DAT scaffold or control (n=3, N=3) after the induction of adipogenic differentiation. Due to cell donor variability in the magnitude of the response, the results for each of the three cell donors are shown separately. Error bars represent the standard deviation in the triplicate samples.

Results of the GPDH enzyme activity study corroborated the gene expression data in terms of the effect of the microenvironment on adipogenesis. Due to the large cell donor variability in terms of the magnitude of the activity levels, the sample data from the three different donors was not pooled, but instead considered independently to assess overall trends between the groups (FIG. 7). According the National Institutes of Health Standard, one of the cell donors was overweight (BMI 29.1) and two were obese (BMI 38.3 and 44.0). The highest levels of activity were generally detected in the DAT samples, indicating that this environment was most conducive to adipogenesis. In general, the GPDH activity increased from 72 h to 7 days, consistent with a progression in fat maturation. With the exception of the DAT group, relatively low activity levels were observed at the 72-h time point. As expected, very low activity levels were found in the non-induced TCPS negative control samples at both time points. Under the experimental conditions tested, the lower the donor BMI, the higher the GPDH activity levels in the DAT scaffolds and TCPS positive controls at 7 days. More specifically, for the BMI 29.1 samples, the GPDH activity increased over 7-fold in the DAT scaffolds from 72 h (10.7±3.6 mU/mg) to 7 days (77.2±13.0 mU/mg). The GPDH activity was higher at 72 h (28.8±1.0 mU/mg) in the DAT scaffolds seeded with cells from the BMI 38.3 donor, increasing approximately 2-fold to 56.9±7.3 mU/mg at 7 days. In the BMI 44.0 cell donor set, the DAT scaffold activity levels were 11.4 f 2.7 mU/mg at 72 h and 29.3±0.8 mU/mg at 7 days. In general, culturing the ASC on Millicell™ filter units in a cellular aggregate devoid of exogenous matrix did not promote adipogenesis, relative to the DAT-scaffolds or monolayer cell culture on TCPS.

DISCUSSION

This example supports the premise that the three-dimensional architecture of the ECM is important in directing the cellular response. Removal of the cellular fraction as described herein substantially preserves the native matrix environment, with only minor changes in the ECM architecture. Thus, the methods described herein are superior to other protocols that require mincing or grinding of the tissues, or collagenase digestion. The SEM imaging clearly showed the preservation of the fine network-type collagens within the processed matrix. The histological staining results indicated that at least a fraction of the vascular architecture was preserved, which may ultimately be of benefit in promoting the organization of infiltrating endothelial cells to vascularize the scaffold.

The gene expression results clearly indicate that the decellularized adipose tissue provides a permissive microenvironment for the adipogenic differentiation of human ASC. It is significant that the seeded ASC expressed relatively high levels of the adipogenic markers PPARγ and CEBPα when cultured in proliferation medium. PPARγ and CEBPα are recognized as the master regulators of adipogenic differentiation [27]. The expression of these two genes, which are cross-regulated and sustained at high levels in adipocytes, is believed to have an essential role in the maintenance of the mature phenotype. These two factors induce other transcription factors, as well as a number of genes associated with the proteins required for lipogenesis [28, 29]. Forced expression of either PPARγ or CEBPα has been shown to be sufficient to induce adipogenesis in non-adipogenic fibroblasts [28, 30]. While MSC can express multi-lineage differentiation markers, they are typically expressed at low levels, and cross-regulate one another to maintain the undifferentiated state [21]. Typically, an inductive medium containing a variety of stimulatory agents is required to promote differentiation towards a specific lineage, and observe higher levels of lineage-specific gene expression, including PPARγ and CEBPα [31]. This trend was clearly observed in the TCPS controls included in the current example. In general, the highest levels of adipogenic gene expression were shown in the induced DAT samples. Lipoprotein lipase (LPL), an early marker of adipogenic differentiation, is an enzyme that plays a role in lipogenesis by facilitating the hydrolysis of triglyercides within capillaries to yield free fatty acids, which can subsequently be transferred into developing adipocytes via the fatty acid binding protein aP2 [32, 33]. The results indicate that differentiation medium is required to induce LPL expression within all of the sample groups, in the time frame of the current study. Future studies may identify whether additional adipogenic markers, such as LPL, are expressed in the non-induced DAT environment at later time points. It is also interesting that under the non-induced conditions, CIV was expressed in the TCPS samples, but not the DAT scaffolds. It is possible that the CIV-rich DAT scaffold environment initiated a negative feedback mechanism that repressed CIV synthesis, similar to the results observed with CI expression by fibroblasts cultured in type-I collagen gels [34]. The adipogenic differentiation medium induced high levels of CIV expression in all groups, consistent with ECM expression patterns during lipogenesis.

The lack of adipogenic gene expression in the non-induced cellular aggregate samples, as well as the lower levels of expression in the induced samples relative to the DAT, demonstrates the importance of the exogenous matrix on adipogenesis. The methodology using the filter units has been commonly employed for chondrogenic cultures. The technique has been shown to promote a more rounded cellular organization, which is beneficial in terms of chondrogenesis [35]. The analysis of CII gene expression was included in the current study to confirm that the culturing methods were not inducing the seeded ASC to produce a more cartilage-like matrix. With further research, this rounded morphology could potentially be advantageous to adipogenesis, based on an extension of the results shown in 2-D studies of osteogenesis versus adipogenesis [36]. However, the inclusion of the DAT scaffold is supported by the fact that the decellularized matrix clearly augments the expression of adipogenic gene and protein markers, and also provides bulk and mechanical integrity to the engineered tissues, critical for volume augmentation applications.

The results of the GPDH protein expression study support the gene expression data, indicating that DAT promotes adipogenesis. In comparing the results to previous work involving decellularized human placenta, much higher levels of GPDH activity were observed in the DAT scaffolds than in constructs comprised of decellularized placenta, which had an average activity level of less than 5 mU/mg at 72 h, 7 days, and 14 days after the induction of differentiation, using the same methods of characterization [20]. This comparison clearly supports that both the ECM composition and architecture play critical roles in directing the cellular response, as the ECM of adipose tissue and placenta contain similar types of collagen, with differing distributions and concentrations [15].

The GPDH data also emphasize the impact of cell donor variability on the observed cellular response. While similar trends are observed between the various culture conditions for the three different donors, the magnitude of the response is highly variable. Based on the three donors studied, there is an inverse relationship between GPDH activity and donor BMI. This result is consistent with the knowledge that obesity is associated with the development of insulin resistance [37, 38]. The inductive medium utilized in the current study incorporates both insulin and the insulin-sensitizing reagent, troglitazone. It is highly probable that the ASC from more obese donors are more resistant to the inductive effects of these stimuli. This fact has profound implications in terms of the development of a universal adipose tissue engineering strategy involving autologous or allogenic ASC. It is possible that with more research, strategies could be developed to overcome these individualized limitations in adipogenic differentiation capacity. The consistency of the trends observed in the current study indicates that it is possible to engineer microenvironments that are more conducive for fat formation, regardless of the cell donor source.

WORKING EXAMPLE 2

Figures 8A, 8B:
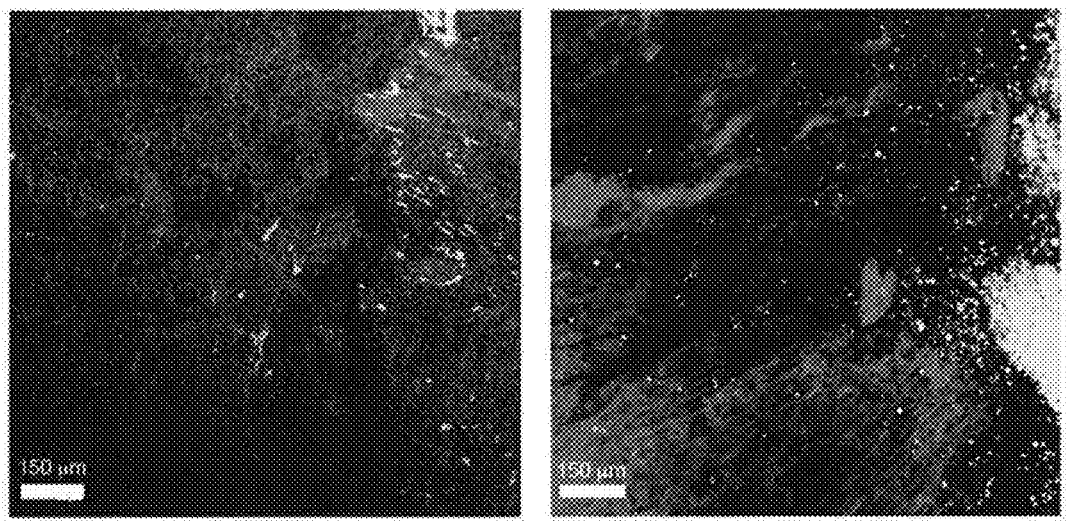
FIG. 8A shows $1\times10^6$ human adipose-derived stem cells (ASC) (in white) seeded on DAT (200 mg) (in gray)
FIG. 8B shows $2.5\times10^6$ ASC (white) seeded on DAT (200 mg) (gray), cultured under hypoxic (5% $O_2$, 37° C.) conditions for 7 days.
Figure 8C:
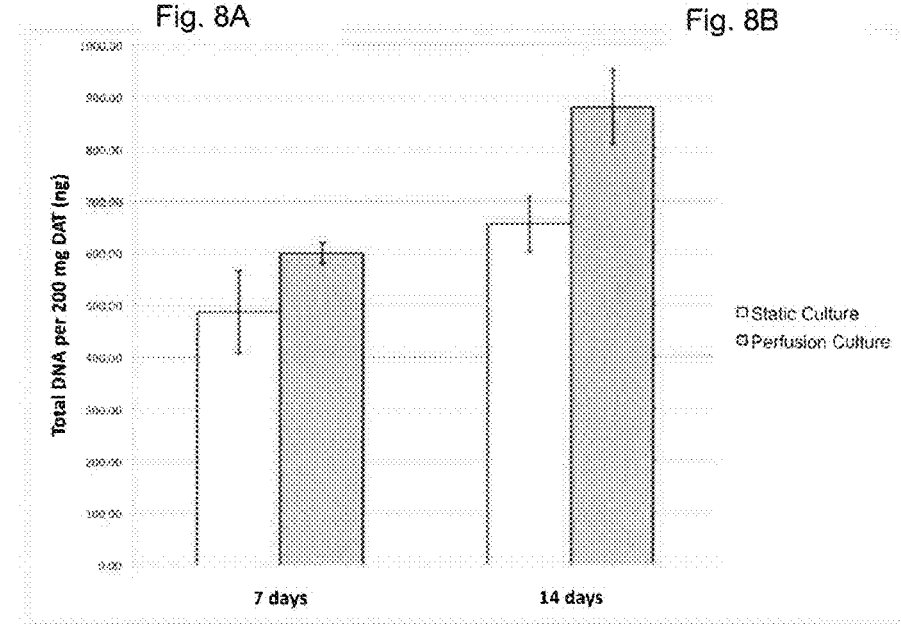
FIG. 8C shows ASC proliferation on DAT scaffolds, measured in terms of the total DNA content. The DAT scaffolds were seeded with ASC and cultured in proliferation medium under either static conditions (white bars) or in a perfusion bioreactor system (gray bars).

Decellularized adipose tissue (DAT) as described herein was used as a culture substrate for adherent cells and, more specifically, for the attachment and proliferation of human adipose-derived stem cells (ASC) on DAT scaffolds. Results in FIGS. 8A and 8B show the ASC labelled with Cell-Tracker™ green (Invitrogen) (shown in white) and the DAT labelled with amine-reactive Alexa fluor 350 carboxylic acid succinimidyl ester (Invitrogen) (shown in gray), to facilitate visualization by confocal microscopy. FIGS. 8A and 8B show representative images of $1 \times 10^6$ ASC seeded on DAT (200 mg), and $2.5 \times 10^6$ ASC seeded on DAT (200 mg), respectively, cultured under hypoxic (5% O2, 37° C.) conditions for 7 days. FIG. 8C shows PicoGreen® (Invitrogen) analysis of ASC proliferation on DAT scaffolds, measured in terms of the total DNA content. The DAT scaffolds (200 mg) were seeded with $1 \times 10^6$ ASC (Passage 2) and cultured in proliferation medium under either static conditions (white bars) or in a perfusion bioreactor system (gray bars) (medium flow rate=1.5 mL/min) to facilitate cell expansion. The data are consistent with proliferation under both conditions, but indicate that higher cell densities were achieved with the perfusion bioreactor system.

WORKING EXAMPLE 3

Preliminary in vive studies of decellularized adipose tissue (DAT) within a subcutaneous implant model were carried out. Canadian Council on Animal Care (CCAC) guidelines were followed. All work was conducted at the Animal Handling Facilities in Botterell Hall at Queen's University. The animal care protocols for this work were reviewed and approved by the Queen's University Animal Care Committee (UACC).

Figure 9A:
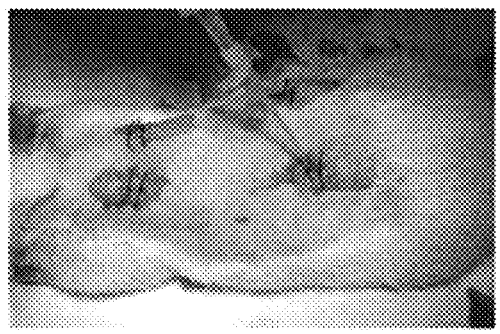
FIGS. 9A to 9F show histological and microscopic data from preliminary in vivo studies of decellularized adipose tissue (DAT) within a subcutaneous implant model. (i) DAT scaffolds (50 mg) and (ii) DAT scaffolds (50 mg) seeded (24 hours prior to implantation) with $1\times10^6$ adipose-derived stem cells (ASCs) isolated from male Wistar rats, were implanted in the subcutaneous space on the dorsa of female Wistar rats (FIG. 9A).
Figure 9B:
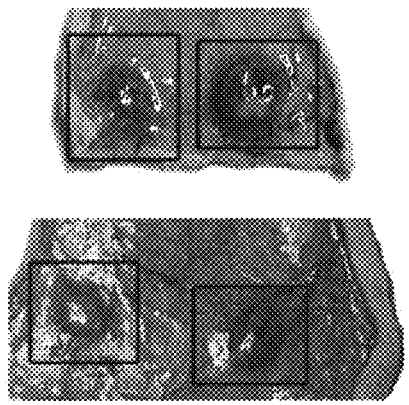
Figure 9C:
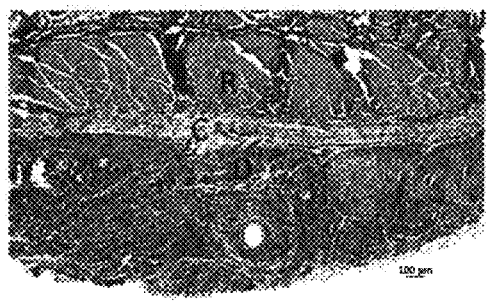
Figure 9D:
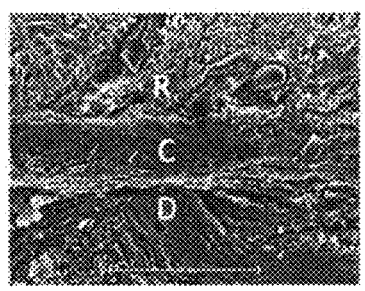
Figure 9E:
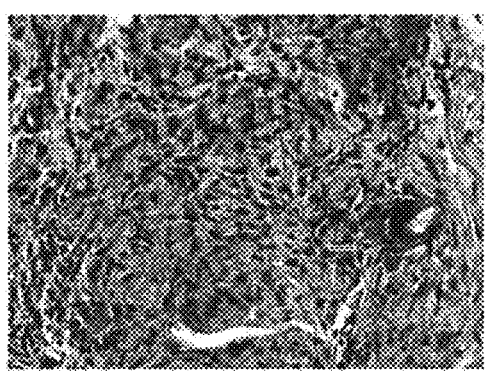
Figure 9F:
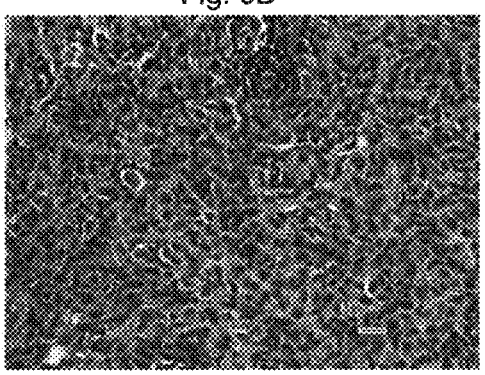

FIGS. 9A to 9F show histological and microscopic data. In these studies (i) DAT scaffolds (50 mg), and (ii) DAT scaffolds (50 mg) seeded (24 hours prior to implantation) with $1 \times 10^6$ adipose-derived stem cells (ASCs) isolated from male Wistar rats, were implanted in the subcutaneous space on the dorsa of female Wistar rats (FIG. 9A). Each rat received two unseeded and two ASC-seeded DAT scaffolds. At 4 days, 7 days, and 14 days post-implantation, the animals were humanely sacrificed and the DAT scaffolds were explanted. Macroscopically, the volume of the DAT scaffolds were well preserved in both groups at all time points, and there was evidence of implant vascularization. FIG. 9B shows images of the ASC-seeded DAT scaffolds at 4 days (top) and 14 days (bottom), with visible blood vessels on the surface of the implants. FIG. 9C shows a representative H&E image of the unseeded DAT scaffold at 14 days (R=rat tissue; C=fibrous capsule; D=DAT scaffold; bar=100 µm) showing macroscopic preservation of the implant volume. The histological results were indicative of normal wound healing, with no evidence of a strong immunogenic response within either group. As the time course progressed, the host response diminished consistent with normal wound healing, with a progressive decrease in the thickness and blood vessel density of the fibrous capsules from 4 days to 14 days in both groups, suggestive that the DAT was becoming integrated into the host. FIG. 9D shows a representative SEM photomicrograph of the unseeded DAT scaffold (D) at 14 days post-implantation (bar=500 µm), showing a relatively thin fibrous capsule (C) and good integration with the host tissues (R). H&E staining of the central regions of the unseeded DAT (FIG. 9E) and ASC-seeded DAT (FIG. 9F) at 14 days showed cellular infiltration, with a higher degree of cellularity in the ASC-seeded DAT scaffolds (bars=20 µm).

WORKING EXAMPLE 4

Figure 10:
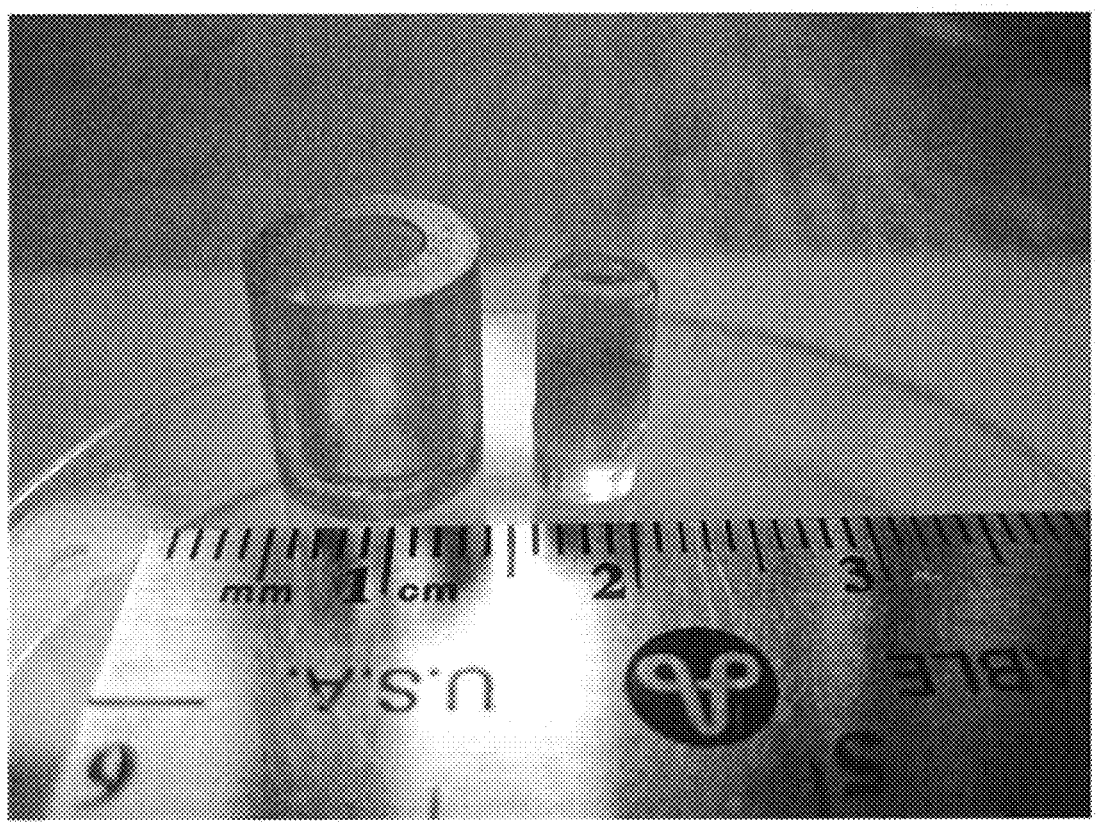
FIG. 10 shows a two-phase composite scaffold comprised of DAT and a hydrogel (photo-crosslinkable methacrylated chondroitin sulphate).

Preliminary studies of a two-phase composite scaffold comprised of decellularized adipose tissue (DAT) and a hydrogel (photo-crosslinkable methacrylated chondroitin sulphate) were carried out. FIG. 10 shows a representative embodiment. The composite chondroitin sulphate+decellularized adipose tissue (CS+DAT) scaffold was fabricated within a mould (6 mm×8 mm), and crosslinked with 320-380 nm UV light at an intensity of 10 mW/cm$^2$ using an EFOS 3000 light source. The composite scaffold had a volume and shape defined by the mould, and macroscopic mechanical properties that were similar to soft tissue.

WORKING EXAMPLE 5

Figure 11A:
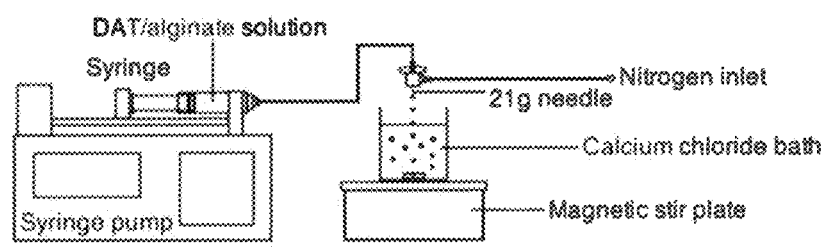
FIGS. 11A and 11B show a method for fabricating spherical microcarriers from decellularized adipose tissue (DAT) using an air-jet droplet technique. Lower panels are SEM photomicrographs showing a macroscopic view of a spherical DAT-based microcarrier (left), the microporous surface topography of the DAT-based microcarriers (centre), and the interior microstructure of the DAT-based microcarriers (right).
Figure 11B:
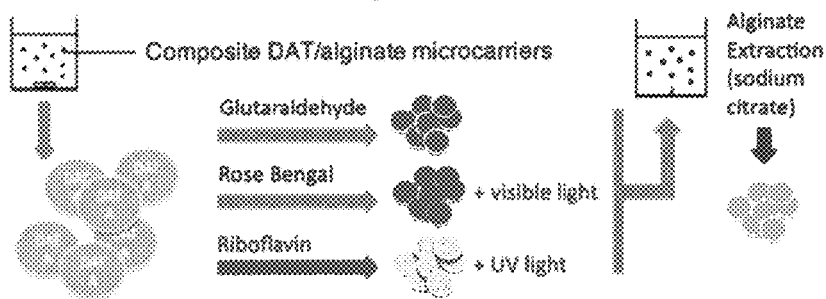
Figure 11B:
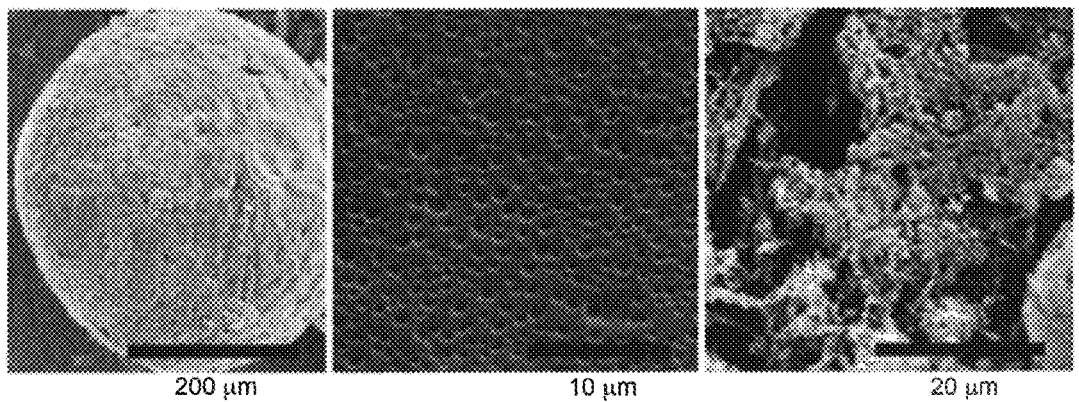

In this example spherical microcarriers were fabricated from decellularized adipose tissue (DAT) using an air-jet droplet technique. The method used in this example is shown schematically in FIGS. 11A and 11B. Briefly, solubilized DAT was temporarily stabilized with a porogen (alginate), the composite beads were crosslinked, and then the porogen was extracted to yield the DAT-based microcarriers. Representative SEM photomicrographs (three lower panels in FIG. 11B) show a macroscopic view of a spherical DAT-based microcarrier (left), the microporous surface topography of a DAT-based microcarrier (centre), and the interior microstructure of a DAT-based microcarrier (right).

Figures 12A, 12B, 12C:
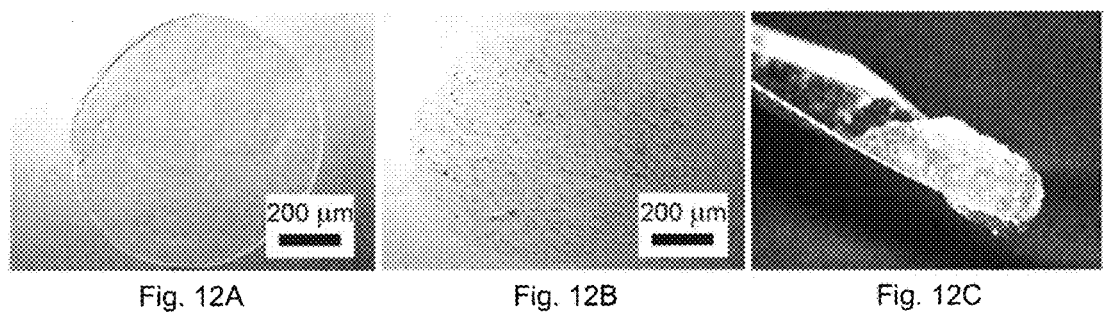
FIG. 12A shows a hydrated DAT-based microcarrier.
FIG. 12B shows a DAT-based microcarrier seeded with human adipose-derived stem cells (ASCs) and cultured for 28 days under dynamic conditions in a spinner flask system.
FIG. 12C shows a macroscopic aggregate of DAT-based microcarriers seeded with human ASCs (after 28 days of dynamic culture), filling a volume of approximately 1 $cm^3$.
Figures 12D, 12E:
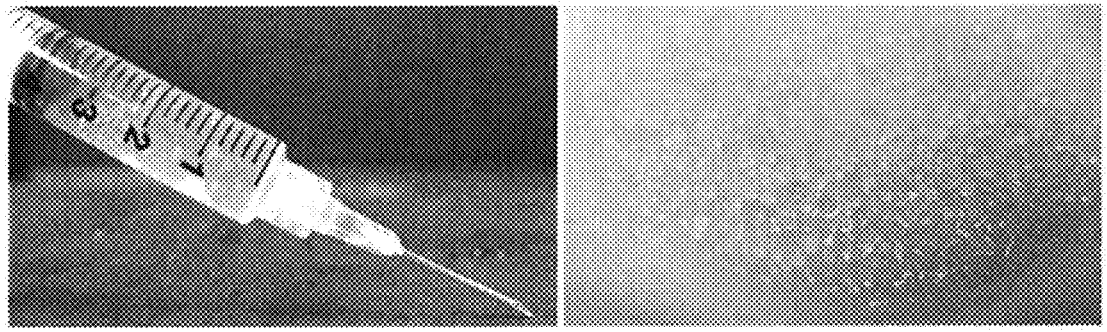
FIG. 12D shows syringe loading of microcarriers with an 18-gauge needle in a minimal fluid volume.
FIG. 12E shows microcarriers post-extrusion through an 18-gauge hypodermic needle.

FIGS. 12A to 12E show hydrated DAT-based microcarrier morphology by optical microscopy, and show the injectability of the DAT-based microcarriers. FIG. 12A shows a hydrated DAT-based microcarrier. FIG. 12B shows a DAT-based microcarrier seeded with human adipose-derived stem cells (ASCs) and cultured for 28 days under dynamic conditions in a spinner flask system. The microcarriers facilitated cell adhesion and demonstrated excellent mechanical integrity over the culture period, with no observable degradation. FIG. 12C shows a macroscopic aggregate of DAT-based microcarriers seeded with human ASCs (after 28 days of dynamic culture), filling a volume of approximately 1 cm$^3$. FIG. 12D shows a syringe loading of microcarriers with an 18-gauge needle in a minimal fluid volume. FIG. 12E shows microcarriers post-extrusion through an 18-gauge hypodermic needle. The DAT-based microcarriers were readily extruded through the needle and were well preserved, with no observable signs of damage or detectable changes in bead size or morphology when assessed using optical and SEM imaging. Depending on the injection site, the extruded microcarriers may form monolayers or larger volume aggregates.

Figure 13:
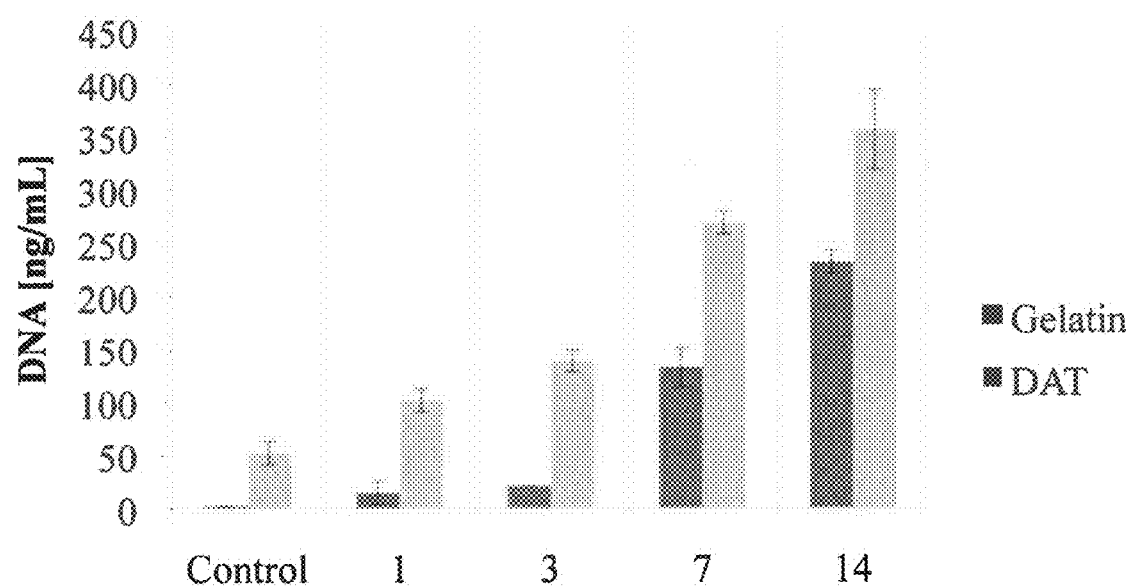
FIG. 13 is a bar graph showing cell proliferation of human ASCs on DAT-based and gelatin-based microcarriers cultured over 14 days in a dynamic spinner flask system, as quantified in terms of total DNA content. Data are presented as the mean ± standard deviation in triplicate samples.

Cell proliferation of human adipose-derived stem cells (ASCs) on DAT-based and gelatin-based microcarriers cultured over 14 days in a dynamic spinner flask system was quantified in terms of total DNA content measured using the PicoGreen assay (Invitrogen). In FIG. 13, data are presented as the mean ± standard deviation in triplicate samples. Higher cell proliferation was measured on the DAT-based microcarriers than on gelatin control microcarriers, fabricated using identical methods.

Figure 14:
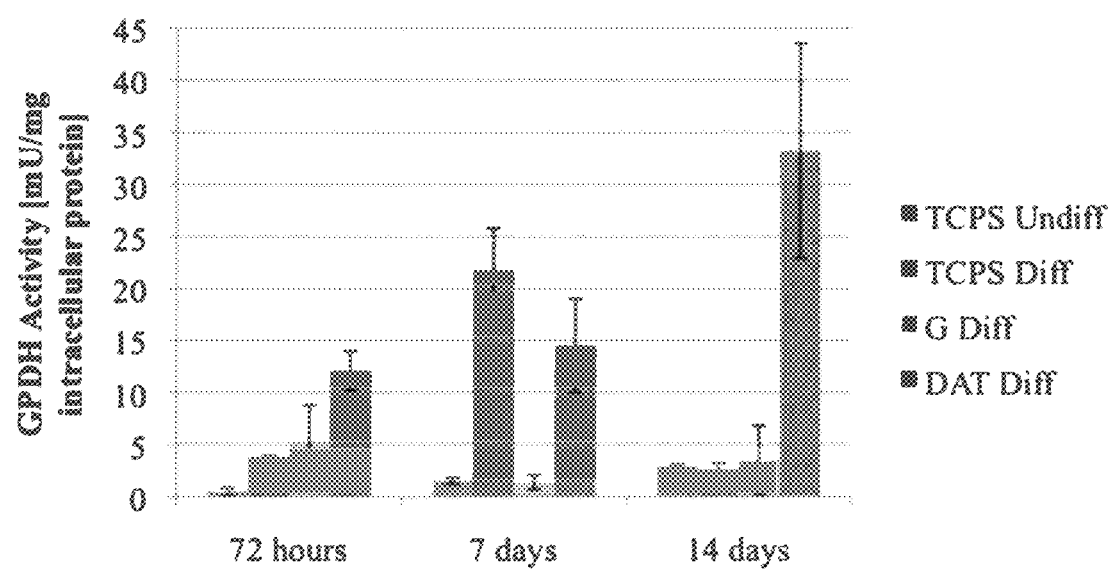
FIG. 14 is a bar graph showing mean glycerol-3-phosphate (GPDH) enzyme activity normalized to total intracellular protein content on DAT-based microcarriers, gelatin (G)-based microcarriers, and tissue culture polystyrene (TCPS) controls seeded with human ASCs and cultured in adipogenic medium. Error bars represent the standard deviation in triplicate samples.

Mean glycerol-3-phosphate (GPDH) enzyme activity normalized to total intracellular protein content was determined for DAT-based microcarriers, gelatin (G)-based microcarriers, and tissue culture polystyrene (TCPS) controls, seeded with human adipose-derived stem cells (ASCs) and cultured in adipogenic medium. Data are shown in FIG. 14 wherein error bars represent the standard deviation in triplicate samples. The data show that the DAT-based microcarriers promoted a stronger adipogenic response, relative to the gelatin-based microcarriers fabricated using identical methods.

Equivalents

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

1. Fernandez E M, Mackley C L. Soft tissue augmentation: a review. J Drugs Dermatol. 2006 July-August; 5(7):630-41.
2. Homicz M R, Watson D. Review of injectable materials for soft tissue augmentation. Facial Plast Surg. 2004 February; 20(1):21-9.
3. Fischbach C, Spruss T, Weiser B, Neubauer M, Becker C, Hacker M, et al. Generation of mature fat pads in vitro and in vivo utilizing 3-D long-term culture of 3T3-L1 preadipocytes. Exp Cell Res. 2004 Oct. 15; 300(1):54-64.
4. Alhadlaq A, Tang M, Mao J J. Engineered adipose tissue from human mesenchymal stem cells maintains predefined shape and dimension: implications in soft tissue augmentation and reconstruction. Tissue Eng. 2005 March-April; 11(3-4):556-66.
5, Flynn L E, Prestwich G D, Semple J L, Woodhouse K A. Proliferation and differentiation of adipose-derived stem cells on naturally derived scaffolds. Biomaterials. 2008 April; 29(12):1862-71.
6. Yang Q, Peng J, Lu S, Huang J, Yao J, Yang F, et al. A cartilage ECM-derived 3-D porous acellular matrix scaffold for in vivo cartilage tissue engineering with PKH26-labeled chondrogenic bone marrow-derived mesenchymal stem cells. Tissue Engineering Part A. 2008 May; 14(5):800-.
7, Zhao Y N, Lin H, Zhang J, Chen B, Sun W J, Wang X, et al. Crosslinked Three-Dimensional Demineralized Bone Matrix for the Adipose-Derived Stromal Cell Proliferation and Differentiation. Tissue Engineering Part A. 2009 January; 15(1):13-21.
8. Choi J S, Yang H J, Kim B S, Kim J D, Lee S H, Lee E K, et al. Fabrication of porous extracellular matrix (ECM) scaffolds from human adipose tissue. Tissue Eng Part C Methods. 2009; E-published ahead of print Jul. 14, 2009.
9. Choi J S, Yang H J, Kim B S, Kim J D, Kim J Y, Yoo B, et al. Human extracellular matrix (ECM) powders for injectable cell delivery and adipose tissue engineering. J Control Release. 2009; 138(1):2-7.
10. Samani A, Bishop J, Luginbuhl C, Plewes D B. Measuring the elastic modulus of ex vivo small tissue samples. Phys Med Biol. 2003 Jul. 21; 48(14):2183-98.
11. Gilbert T W, Sellaro T L, Badylak S F. Decellularization of tissues and organs. Biomaterials. 2006 July; 27(19): 3675-83.
12. Young D A, Ibrahim D O, Hu D, Christman K L. Injectable hydrogel scaffold from decellularized human lipoaspirate. Acta Biomater. 2010 Oct. 16.
13. Rossen G, Elisseeff J H, Nahas Z, Ye Z, Hillel A, inventors; Compositions and methods for implantation of adipose tissue and adipose tissue products patent WO 2009102452. 2009.
14. Brown B N, Fruend J M, Li H, Rubin P J, Reing J E, Jeffries E M, et al. Comparison of Three Methods for the Derivation of a Biologic Scaffold Composed of Adipose Tissue Extracellular Matrix. Tissue Eng Part C Methods. 2010 Nov. 3.
15. Flynn L, Semple J L, Woodhouse K A. Decellularized placental matrices for adipose tissue engineering. J Biomed Mater Res A. 2006 November; 79(2):359-69.
16. Rieder E, Kasimir M T, Silberhumer G, Seebacher G, Wolner E, Simon P, et al. Decellularization protocols of porcine heart valves differ importantly in efficiency of cell removal and susceptibility of the matrix to recellularization with human vascular cells. J Thorac Cardiovasc Surg. 2004 February; 127(2):399-405.
17. Tebb T A, Tsai S, Glattauer V, White J, Ramshaw J A M, Werkmeister J A. Development of porous collagen beads for chondrocyte culture. Cytotechnology. 2006; 52:99-106.
18. Boyle J, Luan B, Cruz T F, Kandel Ra. Characterization of Proteoglycan Accumulation during Formation of Cartilagenous Tissue in-Vitro. Osteoarthritis and Cartilage. 1995 June; 3(2):117-25.
19. Gorzelniak K, Janke J, Engeli S, Sharma A M. Validation of endogenous controls for gene expression studies in human adipocytes and preadipocytes. Horm Metab Res. 2001 October; 33(10):625-7.
20. Flynn L, Prestwich G D, Semple J L, Woodhouse K A. Adipose tissue engineering with naturally derived scaffolds and adipose-derived stem cells. Biomaterials. 2007 September; 28(26):3834-42.
21. Rosen E D, MacDougald O A. Adipocyte differentiation from the inside out. Nat Rev Mol Cell Biol. 2006 December; 7(12):885-96.
22. Nakajima I, Yamaguchi T, Ozutsumi K, Aso H. Adipose tissue extracellular matrix: newly organized by adipocytes during differentiation. Differentiation. 1998 August; 63(4): 193-200.
23. Smas C M, Sul H S. Control of adipocyte differentiation. Biochem J. 1995 Aug. 1; 309(Pt3):697-710.
24. Gronthos S, Franklin D M, Leddy H A, Robey P G, Storms R W, Gimble J M. Surface protein characterization of human adipose tissue-derived stromal cells. Journal of Cellular Physiology. 2001 October; 189(1):54-63.
25. Cheng N C, Estes B T, Awad H A, Guilak F. Chondrogenic differentiation of adipose-derived adult stem cells by a porous scaffold derived from native articular cartilage extracellular matrix. Tissue Eng Part A. 2009 February; 15(2):231-41.
26. Gregoire F M, Smas C M, Sul H S. Understanding adipocyte differentiation. Physiol Rev. 1998 July; 78(3): 783-809.
27. Morrison R F, Farmer S R. Hormonal signaling and transcriptional control of adipocyte differentiation. J Nutr. 2000 December; 130(12):3116S-21S.
28. Ailhaud G. "Development of white adipose tissue and adipocyte differentiation". Klaus S, editor Adipose Tissues. Georgetown, Tex.: Landes Biosciences; 2001. p. 27-35.
29. Lazar M A. Becoming fat. Genes Dev. 2002 January 1; 16(1):1-5.
30. Tontonoz P, Hu E, Spiegelman B M. Stimulation of adipogenesis in fibroblasts by PPAR gamma 2, a lipid-activated transcription factor. Cell. 1994 Dec. 30; 79(7): 1147-56.
31. Zuk P A, Zhu M, Mizuno H, Huang J, Futrell J W, Katz A J, et al. Multilineage cells from human adipose tissue: implications for cell-based therapies. Tissue Eng. 2001 April, 7(2):211-28.
32. Eckel R H. Lipoprotein lipase. A multifunctional enzyme relevant to common metabolic diseases. N Engl J Med. 1989 Apr. 20; 320(16):1060-8.
33. Edens N K, Leibel R L, Hirsch J. Mechanism of free fatty acid re-esterification in human adipocytes in vitro. J Lipid Res. 1990 August; 31(8):1423-31.
34. Eckes B, Mauch C, Huppe G, Krieg T. Down-Regulation of Collagen-Synthesis in Fibroblasts within 3-Dimensional Collagen Lattices Involves Transcriptional and Posttranscriptional Mechanisms. Febs Letters. 1993 Mar. 1; 318(2):129-33.
35. Guilak F, Awad H A, Fermor B, Leddy H A, Gimble J M. Adipose-derived adult stem cells for cartilage tissue engineering. Biorheology. 2004; 41(3-4):389-99.
36. McBeath R, Pirone D M, Nelson C M, Bhadriraju K, Chen C S. Cell shape, cytoskeletal tension, and RhoA regulate stem cell lineage commitment. Dev Cell. 2004 April, 6(4):483-95.
37. Hotamisligil G S, Amer P, Caro I F, Atkinson R L, Spiegelman B M. Increased adipose tissue expression of tumor necrosis factor-alpha in human obesity and insulin resistance. J Clin Invest. 1995 May; 95(5):2409-15.
38. Hotamisligil O S, Peraldi P, Budavari A, Ellis R, White M F, Spiegelman B M. IRS-1-mediated inhibition of insulin receptor tyrosine kinase activity in TNF-alpha- and obesity-induced insulin resistance. Science. 1996 February 2; 271(5249):665-8.

The invention claimed is:

1. A decellularized adipose tissue comprising an extracellular matrix including fibrous collagen and network-type collagen including collagen type IV with basement membrane organization, with well-preserved three-dimensional architecture.

2. The decellularized adipose tissue of claim 1, wherein the decellularized adipose tissue is substantially devoid of intact adipose cells.

3. The decellularized adipose tissue of claim 1, wherein the decellularized adipose tissue is substantially free of immunogenic components.

4. The decellularized adipose tissue of claim 1, including one or more of proteoglycan, glycoprotein, glycosaminoglycan, laminin, or fibronectin.

5. The decellularized adipose tissue of claim 1, for use as a cell culture substrate.

6. The decellularized adipose tissue of claim 5, wherein the cell culture substrate is for cell expansion and/or cell differentiation and/or for the production of bioproducts comprising tissue and one or more proteins.

7. The decellularized adipose tissue of claim 1, comprising at least one additive selected from seeded cells, a biomaterial, a pharmaceutical agent, a hormone, and a growth factor.

8. The decellularized adipose tissue of claim 1, comprising at least one additive selected from a hydrogel and a derivative of one or more of collagen, gelatin, hyaluronan, chondroitin sulphate, chitosan, alginate, silk, fibrin, protein, proteoglycan, glycosaminoglycan, and polysaccharide.

9. The decellularized adipose tissue of claim 1, comprising a hydrogel based on one or more of poly(ethylene glycol) (PEG), polyethylene, polyurethane, polylactic acid (PLA), polyglycolic acid (PGA), and polylactic co-glycolic acid (PLGA.

10. The decellularized adipose tissue of claim 1, wherein the decellularized adipose tissue is digested and solubilized into a liquid.

11. A bioscaffold prepared from the decellularized adipose tissue of claim 1.

12. The bioscaffold of claim 11, for use in a surgical procedure.

13. The bioscaffold of claim 12, wherein the surgical procedure is general surgery, reconstructive surgery, cosmetic surgery, cardiac surgery, orthopaedic surgery, neurosurgery, or urological or gynaecological surgery.

14. The bioscaffold of claim 11, wherein the bioscaffold is used for wound healing applications.

15. The bioscaffold of claim 11, wherein the bioscaffold is used as a hemostatic agent.

16. The bioscaffold of claim 11, comprising one or more materials selected from decellularized extracellular matrix derived from a non-adipose tissue, a synthetic material, a pharmaceutical composition, a hormone, and a growth factor.

17. The bioscaffold of claim 11, wherein the bioscaffold is autologous or allogenic.

18. The bioscaffold of claim 11, wherein the bioscaffold is xenogenic.

19. A scaffold prepared from the decellularized adipose tissue of claim 10.

20. A coating prepared from the decellularized adipose tissue of claim 10.

21. The coating of claim 20, wherein the coating is cross-linked.

22. A microcarrier bead prepared from the decellularized adipose tissue of claim 10.

23. A microcarrier bead including the coating of claim 20.

24. The microcarrier bead of claim 22, for use as a cell and/or drug and/or growth factor delivery vehicle.

25. The microcarrier bead of claim 22, for use as a small volume-bulking agent in cosmetic or reconstructive surgery.

26. The microcarrier bead of claim 22, for use in fabrication of a composite bioscaffold with decellularized adipose tissue.

27. The microcarrier bead of claim 22, wherein the microcarrier bead is cross-linked.

28. The microcarrier bead of claim 22, wherein the microcarrier bead is porous.

29. A particle prepared from the decellularized adipose tissue of claim 1.

30. A particle including the coating of claim 20.

* * * * *